(12) United States Patent
Shimokawa et al.

(10) Patent No.: US 12,359,062 B2
(45) Date of Patent: Jul. 15, 2025

(54) POLYCARBONATE RESIN, METHOD FOR PRODUCING SAME, POLYCARBONATE RESIN COMPOSITION AND MOLDED BODY

(71) Applicant: MITSUBISHI GAS CHEMICAL COMPANY, INC., Tokyo (JP)

(72) Inventors: Keisuke Shimokawa, Tokyo (JP); Hidefumi Harada, Tokyo (JP); Takehiko Isobe, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 637 days.

(21) Appl. No.: 17/760,575

(22) PCT Filed: Sep. 11, 2020

(86) PCT No.: PCT/JP2020/034476
§ 371 (c)(1),
(2) Date: Mar. 15, 2022

(87) PCT Pub. No.: WO2021/054258
PCT Pub. Date: Mar. 25, 2021

(65) Prior Publication Data
US 2022/0356346 A1    Nov. 10, 2022

(30) Foreign Application Priority Data

Sep. 20, 2019 (JP) ................ 2019-171377

(51) Int. Cl.
*C08L 69/00* (2006.01)
*C08G 64/16* (2006.01)
*C08G 64/30* (2006.01)

(52) U.S. Cl.
CPC .............. *C08L 69/00* (2013.01); *C08G 64/16* (2013.01); *C08G 64/307* (2013.01)

(58) Field of Classification Search
CPC ........ C08L 69/00; C08G 64/16; C08G 64/307
See application file for complete search history.

(56) References Cited

U.S. PATENT DOCUMENTS 5,849,859 A * 12/1998 Acemoglu ......... C08G 64/0208
424/278.1
2009/0105393 A1* 4/2009 Jansen .................. C08G 63/64
524/502
2020/0346386 A1* 11/2020 Oh ...................... C08G 63/672

FOREIGN PATENT DOCUMENTS

JP          7-505420 A     6/1995
JP          2017-82234 A   5/2017
KR          2016-0103692 A 9/2016

OTHER PUBLICATIONS

Gawronska, Krystyna. "Synthesis and conformations of 2, 3: 4, 5- and 2, 4: 3, 5-di-O-isopropylidene-D-mannitol." Carbohydrate research 176.1 (1988): 79-85. (Year: 1988).*
Park, J. et al., "Thermally Stable Bio-Based Aliphatic Polycarbonates with Quadra-Cyclic Diol from Renewable Sources", Macromolecular Research, 26, 2018, pp. 246-253.
Zakharova, E. et al., "Sugar-based bicyclic monomers for aliphatic polyesters: a comparative appraisal of acetalized alditols and isosorbide", Designed Monomers and Polymers, 20, 2016, pp. 157-166.
Lavilla, C. et al., "Bio-Based Aromatic Polyesters from a Novel Bicyclic Diol Derived from D-Mannitol", Macromolecules, 45, 2012, pp. 8257-8266.
Marin, R. et al., "Carbohydrate-Based Poly(ester-urethane)s: A Comparative Study Regarding Cyclic Alditols Extenders and Polymerization Procedures", Journal of Applied Polymer Science, 114, 2009, pp. 3723-3736.
International Search Report and Written Opinion of the International Searching Authority issued in International Patent Application No. PCT/JP2020/034476, dated Dec. 1, 2020, along with an English translation thereof.

* cited by examiner

*Primary Examiner* — Ling Siu Choi
(74) *Attorney, Agent, or Firm* — GREENBLUM & BERNSTEIN P.L.C.

(57) ABSTRACT

The present application provides: a polycarbonate resin which has heat resistance and is able to be produced using a starting material that is derived from natural products; and a monomer compound which enables the achievement of this resin. A polycarbonate resin which includes a constituent unit represented by general formula (1); a monomer compound which enables the achievement of this resin; and a polycarbonate resin which includes a constituent unit represented by general formula (1) and a constituent unit represented by general formula (2).

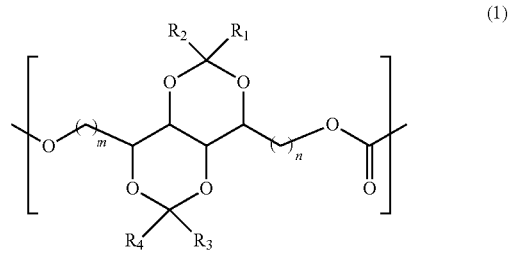

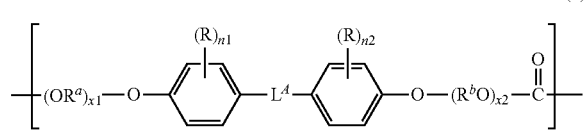

16 Claims, No Drawings

POLYCARBONATE RESIN, METHOD FOR PRODUCING SAME, POLYCARBONATE RESIN COMPOSITION AND MOLDED BODY

TECHNICAL FIELD

The present invention relates to a polycarbonate resin, a method for producing the same, a monomer, a polycarbonate resin composition and a molded body.

BACKGROUND ART

Polycarbonate resins are widely used in electrical and electronic equipments, office automation equipments, optical media, automobile components, building components and the like because of excellent mechanical strength, heat resistance, electrical property, dimensional stability, flame retardance, transparency and the like thereof.

Meanwhile, recently, demands for resins derived from natural materials have been increased because of action for reduction in the environmental load. As one of plastic materials derived from natural materials, a polymer obtained by using a compound produced from a sugar or carbohydrate as a monomer has been attracting attention, and research and development thereof have been promoted. For example, Patent Document 1 describes a biodegradable polyester having a structural unit derived from furandicarboxylic acid. Non-Patent Document 1 describes a polycarbonate having a mannitol skeleton. Non-Patent Documents 2-3 describe polyesters having a mannitol skeleton, isosorbide skeleton or glucitol skeleton. Non-Patent Document 4 describes polyesterurethanes having a glucitol skeleton or isosorbide skeleton. However, since these resins derived from natural materials generally have low heat resistance, there is a room for improvement thereof from a practical viewpoint.

PRIOR ART DOCUMENTS

Patent Documents

Patent Document 1: Japanese Laid-Open Patent Publication No. 2017-82234

Non-Patent Documents

Non-Patent Document 1: Macromol. Res., 26, 246-253 (2018)
Non-Patent Document 2: Macromolecules, 45, 8257-8266 (2012)
Non-Patent Document 3: Designed Monomers and Polymers, 20, 157-166 (2016)
Non-Patent Document 4: Journal of Applied Polymer Science, 114, 3723-3736 (2009)

SUMMARY OF THE INVENTION

It is desired to develop a polycarbonate resin having heat resistance, which can be produced using a raw material derived from a natural material, and a monomer compound which enables the achievement of the resin.

Under such circumstances, the present inventors diligently made researches and found that the above-described problem can be solved by the present invention described below. The present invention is, for example, as described below.

[1] A polycarbonate resin which comprises a structural unit (1) represented by general formula (1):

$$\text{(1)}$$

wherein:
$R_1$, $R_2$, $R_3$ and $R_4$ are each independently selected from the group consisting of a hydrogen atom, an alkyl group having 1 to 10 carbon atoms, an aryl group having 6 to 20 carbon atoms and an alkoxy group having 1 to 10 carbon atoms, and the alkyl group, the aryl group and the alkoxy group of $R_1$, $R_2$, $R_3$ and $R_4$ may be further substituted with a substituent;

$R_1$ and $R_2$, and/or $R_3$ and $R_4$ may be bonded to each other to form, together with a carbon atom to which they are attached, a 3 to 9-membered monocyclic alicyclic ring which may be substituted with a substituent;

provided that there is no case where all of $R_1$, $R_2$, $R_3$ and $R_4$ are a methyl group; and m and n each independently represent an integer of 0 to 5.

[2] A polycarbonate resin which comprises a structural unit (1) represented by general formula (1) and a structural unit (2) represented by general formula (2):

$$\text{(1)}$$

wherein in general formula (1):
$R_1$, $R_2$, $R_3$ and $R_4$ are each independently selected from the group consisting of a hydrogen atom, an alkyl group having 1 to 10 carbon atoms, an aryl group having 6 to 20 carbon atoms and an alkoxy group having 1 to 10 carbon atoms, and the alkyl group, the aryl group and the alkoxy group of $R_1$, $R_2$, $R_3$ and $R_4$ may be further substituted with a substituent;

$R_1$ and $R_2$, and/or $R_3$ and $R_4$ may be bonded to each other to form, together with a carbon atom to which they are attached, a 3 to 9-membered monocyclic alicyclic ring which may be substituted with a substituent; and m and n each independently represent an integer of 0 to 5,

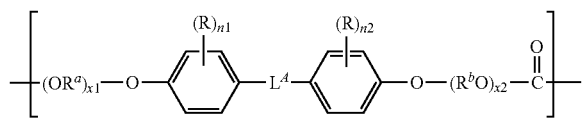

wherein in general formula (2):
$R^a$ and $R^b$ each independently represent an alkylene group having 1 to 8 carbon atoms;
R each independently represents an alkyl group having 1 to 8 carbon atoms or an aryl group having 6 to 12 carbon atoms;
x1 and x2 each independently represent an integer of 0 to 10;
n1 and n2 each independently represent an integer of 0 to 4; and
$L^A$ represents a single bond or a linking group represented by any one of formulae (a) to (g):

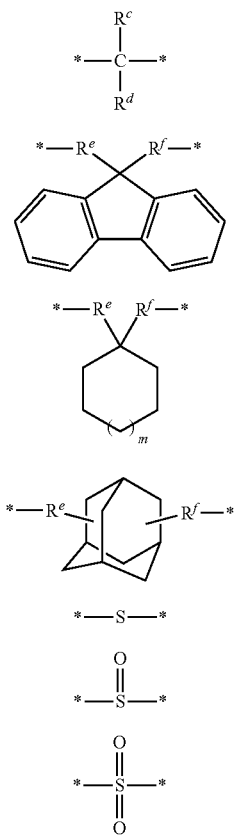

wherein:
* represents a bonding position;
$R^c$ and $R^d$ each independently represent a hydrogen atom, an alkyl group having 1 to 8 carbon atoms or an aryl group having 6 to 12 carbon atoms;
$R^e$ and $R^f$ each independently represent a single bond or an alkylene group having 1 to 4 carbon atoms; and
m represents an integer of 1 to 10.

[3] The polycarbonate resin according to item [2], wherein the content ratio between the structural unit (1) and the structural unit (2) [(1)/(2)] (molar ratio) is 0.01/99.99 to 99.99/0.01.

[3a] The polycarbonate resin according to item [3], wherein the content ratio between the structural unit (1) and the structural unit (2) [(1)/(2)] (molar ratio) is 1/99 to 99/1 (more preferably 10/90 to 90/10, even more preferably 20/80 to 80/20, and particularly preferably 30/70 to 60/40).

[4] The polycarbonate resin according to item [2], [3] or [3a], wherein the structural unit (2) includes at least one derived from a compound selected from the group consisting of 4,4-bis(4-hydroxyphenyl)propane, 2,2-bis(4-hydroxy-3-methylphenyl)propane, 1,1-bis(4-hydroxyphenyl)cyclohexane and 1,1-bis(4-hydroxyphenyl)ethane.

[5] The polycarbonate resin according to any one of items [1] to [4], wherein the content of a remaining phenolic compound is 3000 mass ppm or less relative to 100% by mass of the polycarbonate resin.

[5a] The polycarbonate resin according to any one of items [1] to [4], wherein the content of a remaining by-product alcohol-based compound is 3000 mass ppm or less relative to the polycarbonate resin (100% by mass).

[6] The polycarbonate resin according to any one of items [1] to [5], wherein:
$R_1$, $R_2$, $R_3$ and $R_4$ are each independently selected from the group consisting of a hydrogen atom, an alkyl group having 1 to 3 carbon atoms, an aryl group having 6 to 10 carbon atoms and an alkoxy group having 1 to 3 carbon atoms, and the alkyl group, the aryl group and the alkoxy group of $R_1$, $R_2$, $R_3$ and $R_4$ may be further substituted with a substituent;
$R_1$ and $R_2$, and/or $R_3$ and $R_4$ may be bonded to each other to form, together with a carbon atom to which they are attached, a cyclopentane ring or a cyclohexane ring which may be substituted with a substituent; and
m and n each independently represent an integer of 1 to 3.

[7] The polycarbonate resin according to any one of items [1] to [5], wherein:
both $R_1$ and $R_3$ are a hydrogen atom, $R_2$ and $R_4$ are each independently selected from the group consisting of a hydrogen atom, an alkyl group having 1 to 10 carbon atoms, an aryl group having 6 to 20 carbon atoms and an alkoxy group having 1 to 10 carbon atoms, and the alkyl group, the aryl group and the alkoxy group of $R_2$ and $R_4$ may be further substituted with the substituent;
$R_1$ and $R_2$, and/or $R_3$ and $R_4$ may be bonded to each other to form, together with a carbon atom to which they are attached, a 3 to 9-membered monocyclic alicyclic ring which may be substituted with a substituent; and
m and n each independently represent an integer of 0 to 5.

[7a] The polycarbonate resin according to any one of items [1] to [5] and [7], wherein there is no case where all of $R_1$, $R_2$, $R_3$ and $R_4$ are a methyl atom.

[7b] The polycarbonate resin according to any one of items [1] to [7], wherein there is no case where all of $R_1$, $R_2$, $R_3$ and $R_4$ are a hydrogen atom.

[8] The polycarbonate resin according to any one of items [1] to [7], which has a weight average molecular weight (Mw) of 10,000 to 70,000.

[9] The polycarbonate resin according to any one of items [1] to [8], wherein the structural unit (1) includes at least one of structural units represented by formulae 1 to 8:

5
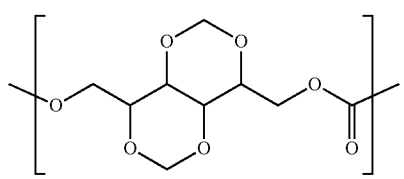
1
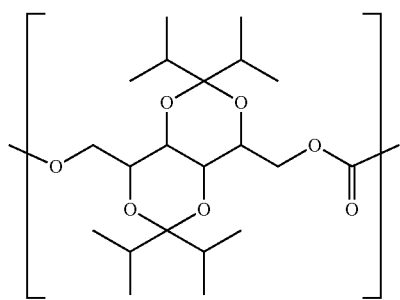
2
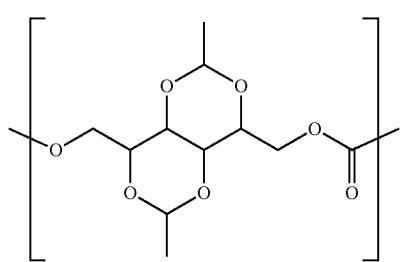
3
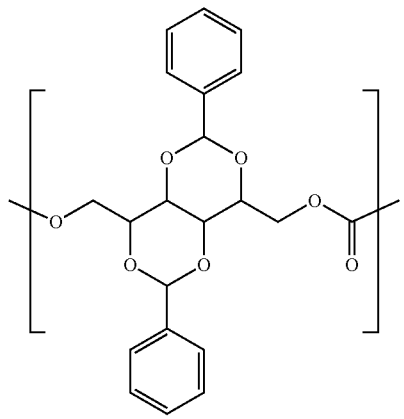
4
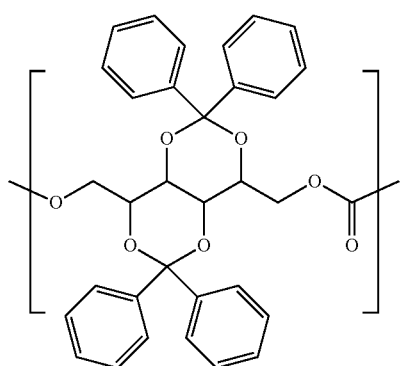
5
6
-continued
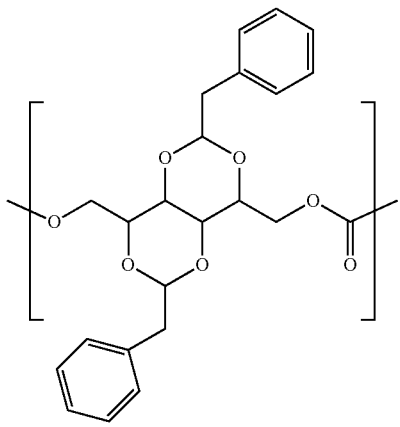
6
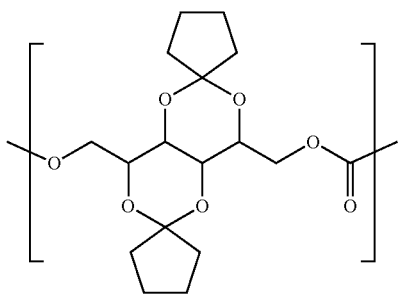
7
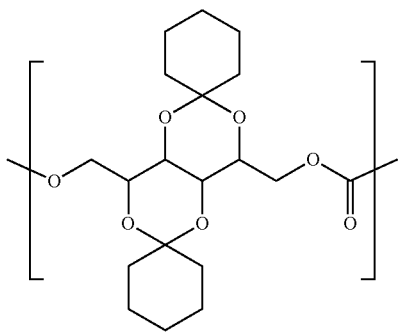
8
[9a] The polycarbonate resin according to any one of items [1] to [8], wherein the structural unit (1) includes at least one of structural units represented by formulae 1 to 9:
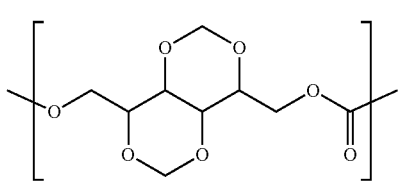
1

2

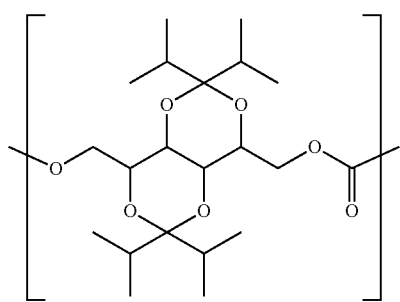

3

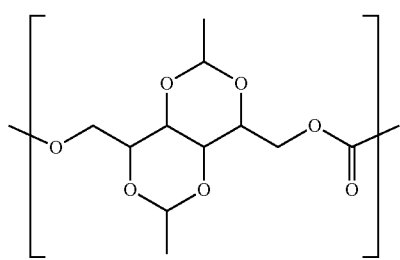

4

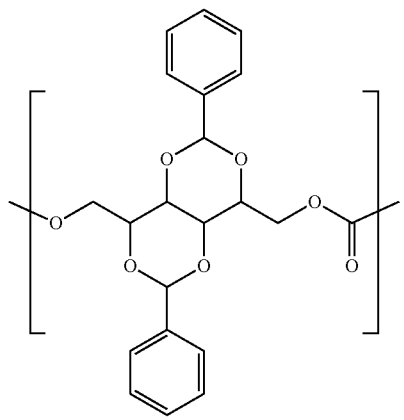

5

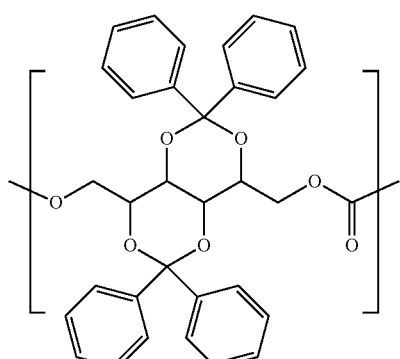

6

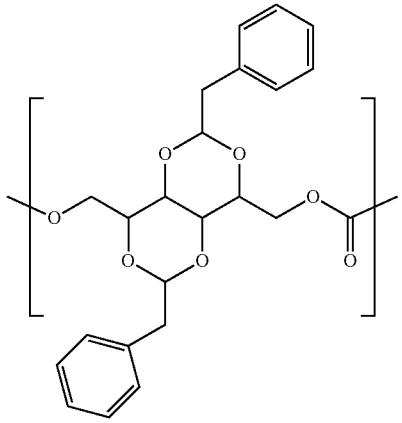

7

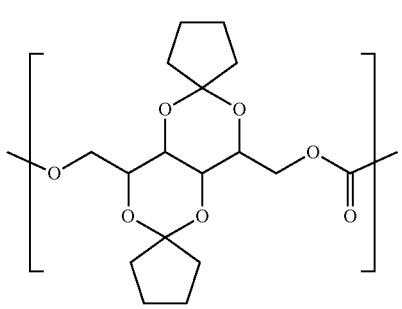

8

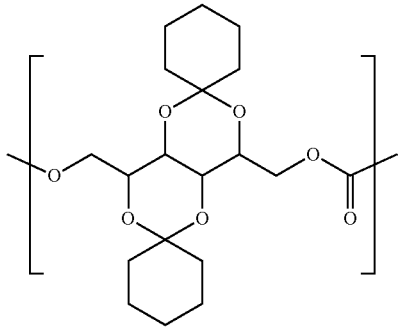

9

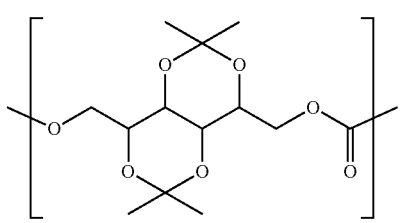

[9b] The polycarbonate resin according to item [9] or [9a], wherein the structural unit (1) includes at least one of structural units represented by formulae 1, 2 and 7 above.

[9c] The polycarbonate resin according to item [9], [9a] or [9b], which is selected from:
 a homopolymer consisting of a structural unit represented by formula 4 above;
 a homopolymer consisting of a structural unit represented by formula 1 above;
 a copolymer which comprises the structural unit (1) including a structural unit represented by formula 9 above and the structural unit (2);
 a copolymer which comprises a structural unit represented by formula 9 above and the structural unit (2);

a copolymer which comprises the structural unit (1) including a structural unit represented by formula 4 above and the structural unit (2);

a copolymer which comprises a structural unit represented by formula 4 above and the structural unit (2);

a copolymer which comprises the structural unit (1) including a structural unit represented by formula 1 above and the structural unit (2); and a copolymer which comprises a structural unit represented by formula 1 above and the structural unit (2).

[10] The polycarbonate resin according to any one of items [1] to [9], which has a glass transition temperature (Tg) of 80 to 250° C.

[11] The polycarbonate resin according to any one of items [1] to [10], wherein the thermal decomposition temperature (5% weight reduction temperature) of the polycarbonate resin is 325° C. or higher.

[12] The polycarbonate resin according to any one of items [1] to [11], wherein the structural unit (1) is obtained from a monomer derived from a natural sugar.

[13] A polycarbonate resin composition comprising the polycarbonate resin according to any one of items [1] to [12].

[14] A molded body obtained by molding the polycarbonate resin composition according to item [12].

[15] A method for producing the polycarbonate resin according to any one of items [1] to [12], which comprises a step of performing a transesterification reaction.

[16] The method according to item [15], wherein the transesterification reaction is performed under a reduced pressure of 1 kPa or less and at a temperature of 260° C. or higher (preferably 260 to 350° C.).

[17] A compound represented by general formula (1)':

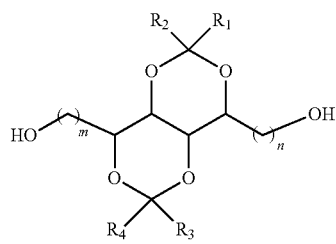

(1)' wherein:
R$_1$, R$_2$, R$_3$ and R$_4$ are each independently selected from the group consisting of a hydrogen atom, an alkyl group having 1 to 10 carbon atoms, an aryl group having 6 to 20 carbon atoms and an alkoxy group having 1 to 10 carbon atoms, and the alkyl group, the aryl group and the alkoxy group of R$_1$, R$_2$, R$_3$ and R$_4$ may be further substituted with a substituent;
provided that there is no case where all of R$_1$, R$_2$, R$_3$ and R$_4$ are a hydrogen atom;
R$_1$ and R$_2$, and/or R$_3$ and R$_4$ may be bonded to each other to form, together with a carbon atom to which they are attached, a 3 to 9-membered monocyclic alicyclic ring which may be substituted with a substituent; and
m and n each independently represent an integer of 0 to 5.

A polycarbonate resin having heat resistance, which can be produced using a raw material derived from a natural material, and a monomer compound which enables the achievement of the resin are provided.

A polycarbonate resin according to a preferred embodiment has more excellent heat resistance (e.g., a high glass transition temperature (Tg) and/or thermal decomposition temperature (5% weight reduction temperature)) when compared to conventional sugar-derived polycarbonate resins, and can be applied to various intended uses including cases and interior and exterior materials of electronic equipments, automobiles, etc.

BEST MODE FOR CARRYING OUT THE INVENTION

Hereinafter, the present invention will be described in detail by way of embodiments, examples, etc., but the present invention is not limited to embodiments, examples, etc. described below and can be arbitrarily changed and then practiced within a range not departing from the gist of the present invention.

Polycarbonate Resin

One embodiment of the present invention relates to a polycarbonate resin which comprises a structural unit (1) represented by general formula (1):

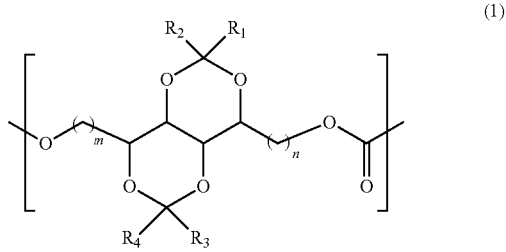

(1)

The polycarbonate resin of this embodiment has the structural unit (1) including a tetrahydro-[1,3]dioxyno[5,4-d][1,3]dioxin-4,8-diyl structure as represented by general formula (1) above. It is considered that, when employing a polycarbonate resin having such a structure, heat resistance (high glass transition temperature (Tg) and/or thermal decomposition temperature (5% weight reduction temperature)) is improved because of possession of a ring structure in the main chain. Moreover, the structural unit (1) can be obtained from a monomer derived from a natural sugar (e.g., mannitol and glucitol), and the polycarbonate resin of this embodiment is preferred from the viewpoint of reduction in the environmental load.

In the polycarbonate resin, as the structural unit (1), one type may be used solely, or two or more types may be used in combination.

In the case where the polycarbonate resin is a copolymer comprising two or more types of structural units, the copolymer may have a structure of either a random copolymer, block copolymer or alternating copolymer.

In formula (1) above, m and n each independently represent an integer of 0 to 5. From the viewpoint of the improvement of heat resistance, m and n are each independently preferably 1 to 3, more preferably 1 to 2, and particularly preferably 1. m and n may be the same or different from each other. In one embodiment, m and n are the same integer (preferably 0 to 5, more preferably 1 to 3, even more preferably 1 to 2, and particularly preferably 1).

In formula (1) above, R$_1$, R$_2$, R$_3$ and R$_4$ (hereinafter also referred to as "R$_1$ to R$_4$") are each independently selected from the group consisting of a hydrogen atom, an alkyl group, an aryl group and an alkoxy group.

$R_1$, $R_2$, $R_3$ and $R_4$ may be the same or different from each other. In one embodiment, $R_1$ and $R_3$ are the same and $R_2$ and $R_4$ are the same. By possession of such a structure, the packing property of a polymer chain is improved, and heat resistance can be improved. In one embodiment, $R_1$ to $R_4$ are the same group.

The aforementioned alkyl group of $R_1$ to $R_4$ may be linear, cyclic or branched. From the viewpoint of the improvement of heat resistance, it is preferably a linear, cyclic or branched alkyl group having 1 to 10 carbon atoms (preferably 1 to 6 carbon atoms, more preferably 1 to 3 carbon atoms, and even more preferably 1 to 2 carbon atoms), more preferably a linear or branched alkyl group having 1 to 10 carbon atoms (preferably 1 to 6 carbon atoms, more preferably 1 to 3 carbon atoms, and even more preferably 1 to 2 carbon atoms), even more preferably a linear alkyl group having 1 to 10 carbon atoms (preferably 1 to 6 carbon atoms, more preferably 1 to 3 carbon atoms, and even more preferably 1 to 2 carbon atoms), and particularly preferably a methyl. Examples of the alkyl group include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, a 2-ethylhexyl group, a cyclopropyl group, a cyclobutyl group, a cyclopentyl group, a cyclohexyl group, a cycloheptyl group, a cyclooctyl group and a cyclononyl group.

Examples of the aforementioned aryl group of $R_1$ to $R_4$ include an aryl group having 6 to 20 carbon atoms (preferably 6 to 10 carbon atoms, more preferably 6 to 10 carbon atoms, and even more preferably 6 carbon atoms). Examples of the aryl group include a phenyl group, a naphthyl group (1-naphthyl group, 2-naphthyl group), an indenyl group, a biphenyl group, an anthryl group and a phenanthryl group. From the viewpoint of heat resistance, the aryl group is preferably selected from a phenyl group and a naphthyl group, and is particularly preferably a phenyl group.

Examples of the aforementioned alkoxy group of $R_1$ to $R_4$ include an alkoxy group having 1 to 10 carbon atoms (preferably 1 to 6 carbon atoms, more preferably 1 to 3 carbon atoms, and even more preferably 1 to 2 carbon atoms). Examples of the alkoxy group include a methoxy group, an ethoxy group, a propoxy group, a butoxy group and a pentyloxy group. From the viewpoint of heat resistance, the alkoxy group is preferably selected from a methoxy group and an ethoxy group.

At least one hydrogen atom in the alkyl group, the aryl group and the alkoxy group of $R_1$ to $R_4$ may be further substituted with a substituent. Note that in the definitions of the preferred numbers of carbons described above with respect to the alkyl group, the aryl group and the alkoxy group of $R_1$ to $R_4$, the numbers of carbons in substituents which may be arbitrarily possessed by the alkyl group, the aryl group and the alkoxy group are not included.

Examples of the substituent include a linear or branched alkyl group having 1 to 20 (preferably 1 to 10, more preferably 1 to 5, and even more preferably 1 to 3) carbon atoms, an alkoxy group having 1 to 20 (preferably 1 to 10, more preferably 1 to 5, and even more preferably 1 to 3) carbon atoms, a thioalkyl group having 1 to 20 (preferably 1 to 10, more preferably 1 to 5, and even more preferably 1 to 3) carbon atoms, a cycloalkyl group having 3 to 20 (preferably 5 to 15, and more preferably 5 to 10) ring-forming carbon atoms, a dialkylamino group having an alkyl group having 1 to 20 (preferably 1 to 10, more preferably 1 to 5, and even more preferably 1 to 3) carbon atoms, an amino group, an aryl group having 6 to 20 (preferably 6 to 18, more preferably 6 to 12, even more preferably 6 to 10, and still more preferably 6) ring-forming atoms, a heteroaryl group having 3 to 20 (preferably 5 to 16) ring-forming atoms, a hydroxy group, a cyano group (CN) and a halogen atom (F, Cl, Br, I). Among them, as the substituent, an aryl group and an alkyl group are preferred.

Alternatively, in formula (1) above, $R_1$ and $R_2$, and/or $R_3$ and $R_4$ may be bonded to each other to form, together with a carbon atom to which they are attached, a 3 to 9-membered monocyclic alicyclic ring which may be substituted with a substituent.

Examples of the 3 to 9-membered monocyclic alicyclic ring include a cyclopropane ring, a cyclobutane ring, a cyclopentane ring, a cyclohexane ring, a cycloheptane ring, a cyclooctane ring and a cyclononane ring. Among them, from the viewpoint of the improvement of the strength of resin molded bodies, a 5 to 8-membered (more preferably 5 to 7-membered) monocyclic alicyclic ring is preferred, a cyclopentane ring or a cyclohexane ring is more preferred, and a cyclohexane ring is particularly preferred.

Examples of the substituent of the alicyclic ring include the above-described substituents for the alkyl group, the aryl group and the alkoxy group of $R_1$ to $R_4$. Among them, as the substituent, an aryl group and an alkyl group are preferred.

In one embodiment, there is no case where all of $R_1$, $R_2$, $R_3$ and $R_4$ in formula (1) above are a methyl atom. In a specific embodiment, the polycarbonate resin consists of only the structural unit represented by formula (1) above.

In one embodiment, in formula (1) above, $R_1$ to $R_4$ are selected from a linear, cyclic or branched alkyl group having 1 to 10 carbon atoms (preferably 1 to 6 carbon atoms, more preferably 1 to 3 carbon atoms, and even more preferably 1 to 2 carbon atoms), an aryl group having 6 to 20 carbon atoms (preferably 6 to 10 carbon atoms, and more preferably 6 carbon atoms) and an alkoxy group having 1 to 10 carbon atoms (preferably 1 to 6 carbon atoms, more preferably 1 to 3 carbon atoms, and even more preferably 1 to 2 carbon atoms), and the alkyl group may be substituted with an aryl group having 6 to 20 carbon atoms (preferably 6 to 10 carbon atoms, and more preferably 6 carbon atoms).

Alternatively, in formula (1) above, $R_1$ and $R_2$, and/or $R_3$ and $R_4$ may be bonded to each other to form, together with a carbon atom to which they are attached, a 3 to 9-membered (more preferably 5 to 7-membered, and particularly preferably 6-membered) monocyclic alicyclic ring.

In one embodiment, in formula (1) above, $R_1$ to $R_4$ are each independently selected from the group consisting of a hydrogen atom, an alkyl group having 1 to 3 carbon atoms (preferably 1 to 2 carbon atoms, and more preferably one carbon atom), an aryl group having 6 to 10 carbon atoms (preferably 6 to 10 carbon atoms, and more preferably 6 carbon atoms) and an alkoxy group having 1 to 3 carbon atoms (preferably 1 to 2 carbon atoms), and the alkyl group, the aryl group and the alkoxy group of $R_1$, $R_2$, $R_3$ and $R_4$ may be further substituted with the above-described substituent, $R_1$ and $R_2$, and/or $R_3$ and $R_4$ may be bonded to each other to form, together with a carbon atom to which they are attached, a cyclopentane ring or a cyclohexane ring which may be substituted with a substituent.

In one embodiment, in formula (1) above, $R_1$ to $R_4$ are each independently selected from a hydrogen atom, an alkyl group having 1 to 3 carbon atoms, a phenyl group and a benzyl group, or alternatively, $R_1$ and $R_2$, and/or $R_3$ and $R_4$ may be bonded to each other to form, together with a carbon atom to which they are attached, a cyclopentane ring or a cyclohexane ring.

In one embodiment, in formula (1) above, $R_1$ to $R_4$ are the same and are selected from a hydrogen atom, an alkyl group having 1 to 3 carbon atoms, a phenyl group, a benzyl group and a naphthyl group. More preferably, $R_1$ to $R_4$ are the same and are selected from a hydrogen atom, an n-propyl group, an ethyl group and a methyl group.

In one embodiment, in formula (1) above, $R_1$ to $R_4$ are the same and are selected from a hydrogen atom and a methyl group. In one embodiment, $R_1$ to $R_4$ are the same and are a hydrogen atom.

In one embodiment, in formula (1) above, both $R_1$ and $R_3$ are a hydrogen atom, $R_2$ and $R_4$ are each independently selected from the group consisting of a hydrogen atom, an alkyl group having 1 to 10 carbon atoms (preferably 1 to 3 carbon atoms, more preferably 1 to 2 carbon atoms, and even more preferably one carbon atom), an aryl group having 6 to 20 carbon atoms (preferably 6 to 10 carbon atoms, and more preferably 6 carbon atoms) and an alkoxy group having 1 to 10 carbon atoms (preferably 1 to 3 carbon atoms, more preferably 1 to 2 carbon atoms, and even more preferably one carbon atom), and the alkyl group, the aryl group and the alkoxy group of $R_2$ and $R_4$ may be further substituted with the above-described substituent, $R_1$ and $R_2$, and/or $R_3$ and $R_4$ may be bonded to each other to form, together with a carbon atom to which they are attached, a 3 to 9-membered (more preferably 5 to 7-membered, and particularly preferably 6-membered) monocyclic alicyclic ring which may be substituted with a substituent.

In this embodiment, m and n each independently represent an integer of 0 to 5 (preferably 1 to 3, more preferably 1 to 2, and even more preferably 1).

When employing the structure of formula (1), a monomer is easily produced, and it is excellent in terms of cost.

In one embodiment, in formula (1) above, $R_1$ and $R_3$ are the same and are selected from a hydrogen atom, an alkyl group having 1 to 3 carbon atoms, a phenyl group and a benzyl group, and $R_2$ and $R_4$ are the same and are selected from an alkyl group having 1 to 3 carbon atoms, a phenyl group, a benzyl group and a naphthyl group. Preferably, both $R_1$ and $R_3$ are a hydrogen atom, and $R_2$ and $R_4$ are the same and are a phenyl group or a naphthyl group. More preferably, both $R_1$ and $R_3$ are a hydrogen atom, and both $R_2$ and $R_4$ are a phenyl group.

In one embodiment, in formula (1) above, $R_1$ and $R_2$, and $R_3$ and $R_4$ are bonded to each other to form, together with a carbon atom to which they are attached, a cyclopentane ring.

In one embodiment, in formula (1) above, $R_1$ and $R_2$, and $R_3$ and $R_4$ are bonded to each other to form, together with a carbon atom to which they are attached, a cyclohexane ring.

In one embodiment, in formula (1) above, there is no case where all of $R_1$, $R_2$, $R_3$ and $R_4$ are a hydrogen atom.

Hereinafter, specific examples of the structural unit (1) will be described.

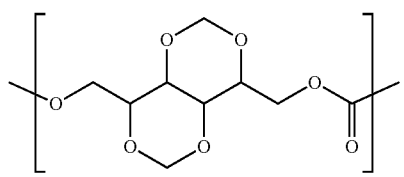

1

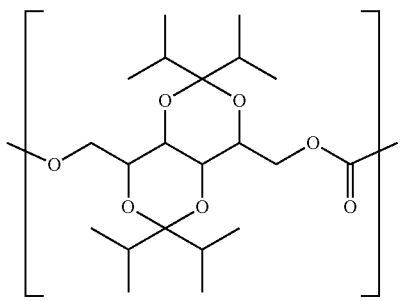

2

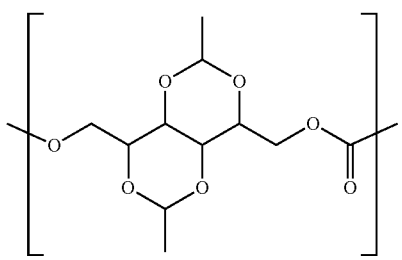

3

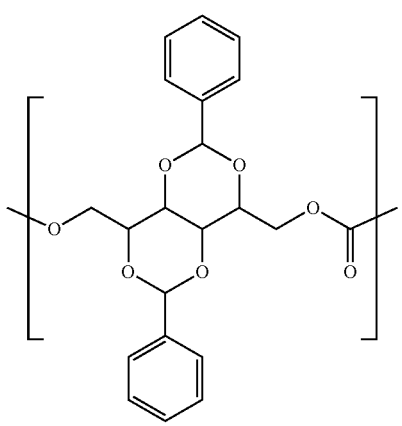

4

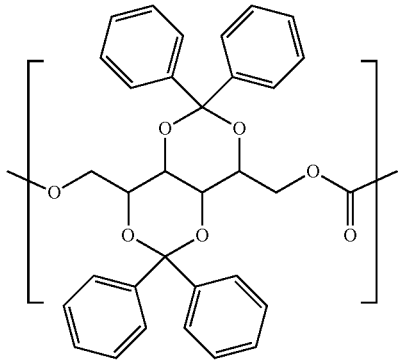

5

-continued

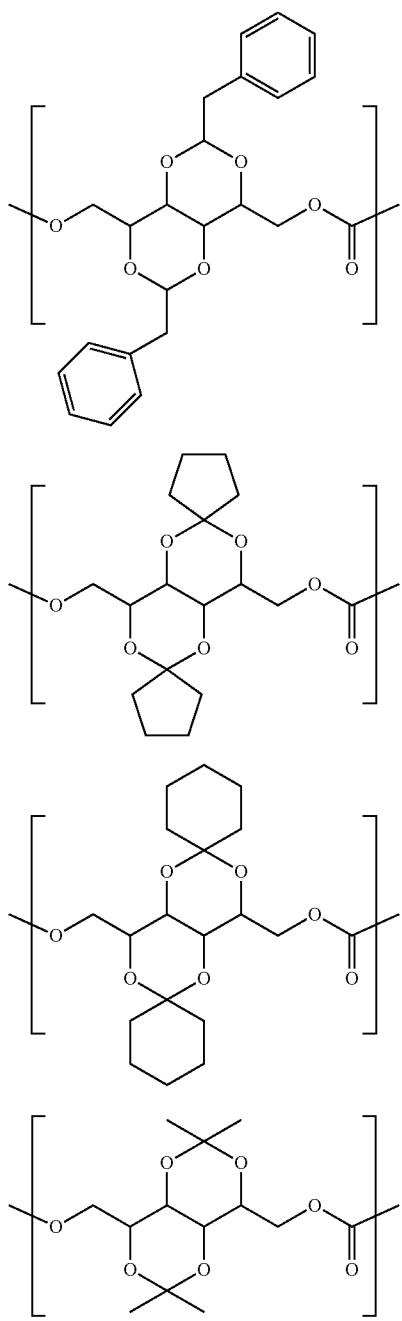

In one embodiment, the structural unit (1) includes at least one of structural units represented by formulae 1 to 9 above.

In one embodiment, the structural unit (1) includes at least one of structural units represented by formulae 1 to 8 above.

In one embodiment, the structural unit (1) includes at least one of structural units represented by formulae 2 to 9 above.

In one embodiment, the structural unit (1) includes at least one of structural units represented by formulae 2 to 8 above.

In one embodiment, the structural unit (1) includes at least one of structural units represented by formulae 1 to 9 above.

In one embodiment, the structural unit (1) includes a structural unit represented by formula 9 above.

In one embodiment, the structural unit (1) includes a structural unit represented by formula 4 above. In one embodiment, the polycarbonate resin is a homopolymer consisting of the structural unit represented by formula 4 above.

In one embodiment, the structural unit (1) includes a structural unit represented by formula 1 above. In one embodiment, the polycarbonate resin is a homopolymer consisting of the structural unit represented by formula 1 above.

The structural unit (1) includes a stereoisomer having a different configuration of oxygen atoms. For example, the below-described structural unit (1a) is a structural unit obtained from a diol structure derived from D-mannose, and the below-described structural unit (1b) is a structural unit obtained from a diol structure derived from D-glucose.

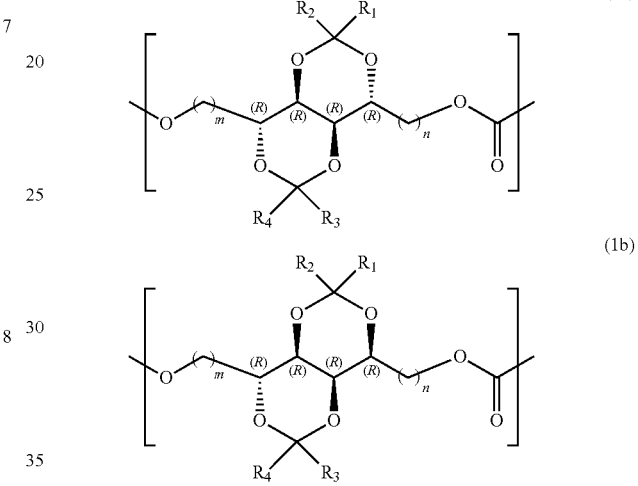

In general formulae (1a) and (1b) above, $R_1$, $R_2$, $R_3$, $R_4$, m and n are the same as those in the aforementioned definitions with respect to general formula (1), and preferred embodiments thereof are also the same as described above.

In the present invention, the structural unit (1) may be composed of a unit having a single three-dimensional structure, or may be composed of a unit having a plurality of different three-dimensional structures. For example, the structural unit (1) may be composed of only the above-described structural unit (1a), or may be composed of only the above-described structural unit (1b), or may be composed of a mixture of the structural unit (1a) and the structural unit (1b), or may be composed of a mixture of the structural unit (1a), the structural unit (1b) and another structural unit having another three-dimensional structure. When employing a mixture, the ratio between structural units is not particularly limited. In the present invention, regarding the structural unit (1) represented by formula (1) above, a compound (1)' represented by formula (1)' which will be described later, and specific examples thereof described as preferred embodiments, when there is no description with respect to stereoisomerism, both the case where it is composed of a unit having a single three-dimensional structure and the case where it is composed of a unit having a plurality of different three-dimensional structures are included.

Note that when it is to be composed of a unit having a single three-dimensional structure, as a monomer raw material, a monomer compound whose three-dimensional structure is controlled may be used.

The polycarbonate resin may further comprise a structural unit (2) represented by general formula (2) below. Specifically, one embodiment of the present invention is a polycarbonate resin which comprises the structural unit (1) represented by general formula (1) and the structural unit (2) represented by general formula (2).

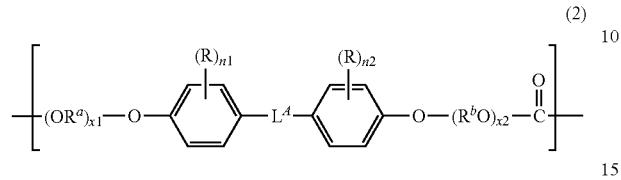

(2)

In formula (2) above, $R^a$ and $R^b$ each independently represent an alkylene group having 1 to 8 carbon atoms (preferably 1 to 5 carbon atoms, more preferably 2 to 3 carbon atoms, and even more preferably 2 carbon atoms).

The alkylene group may be either a linear alkylene group or a branched alkylene group, and examples thereof include a methylene group (—$CH_2$—), an ethylene group (—$CH_2CH_2$—), an ethylidene group (—$CH(CH_3)$—), a trimethylene group (—$CH_2CH_2CH_2$—), a propylene group (—$CH(CH_3)CH_2$—), a propylidene group (—$CHCH_2(CH_3)$—), an isopropylidene group (—$C(CH_3)_2$—), a tetramethylene group (—$CH_2CH_2CH_2CH_2$—), a 1-methyltrimethylene group (—$CH(CH_3)CH_2CH_2$—), a 2-methyltrimethylene group (—$CH_2CH(CH_3)CH_2$—), a butylene group (—$C(CH_3)_2CH_2$—), and a group represented by —$(CH_2)_n$— (n represents an integer of 1 to 8, and preferably an integer of 1 to 5).

Further, in formula (2) above, R each independently represents an alkyl group having 1 to 8 carbon atoms (preferably 1 to 5 carbon atoms, more preferably 1 to 3 carbon atoms, and even more preferably one carbon atom) or an aryl group having 6 to 12 (preferably 6 to 10, and more preferably 6) ring-forming carbon atoms. Specific examples of the alkyl group and aryl group include the same alkyl group and aryl group as those which can be selected as $R_1$ to $R_4$ in general formula (1).

In formula (2) above, x1 and x2 each independently represent an integer of 0 to 10, preferably an integer of 0 to 5, more preferably an integer of 0 to 2, and even more preferably 0.

In formula (2) above, n1 and n2 each independently represent an integer of 0 to 4, preferably 0 to 2, more preferably 0 to 1, and even more preferably 0.

In formula (2) above, $L^A$ represents a single bond or a linking group represented by any one of formulae (a) to (g):

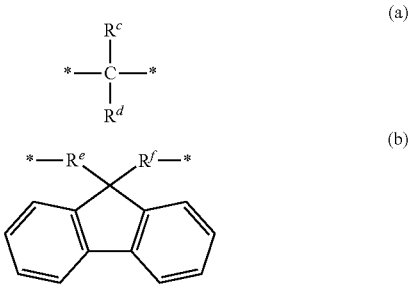

(a)

(b)

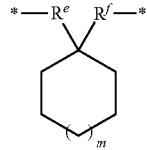

(c)

(d)

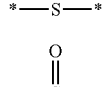

(e)

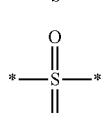

(f)

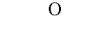

(g)

In formulae (a) to (g) above, * represents a bonding position.

In formula (a) above, $R^c$ and $R^d$ each independently represent a hydrogen atom, an alkyl group having 1 to 8 carbon atoms (preferably 1 to 5 carbon atoms, more preferably 1 to 3 carbon atoms, and even more preferably one carbon atom) or an aryl group having 6 to 12 carbon atoms (preferably 6 to 10 carbon atoms, and more preferably 6 carbon atoms).

Examples of the alkyl group and the aryl group include the same alkyl group and aryl group as those which can be selected as R in formula (2) above.

In formulae (b) to (d) above, $R^e$ and $R^f$ each independently represent a single bond or an alkylene group having 1 to 4 carbon atoms (preferably 1 to 2 carbon atoms, and more preferably one carbon atom).

Examples of the alkylene group include the same alkylene group having 1 to 4 carbon atoms as that which can be selected as $R^a$ and $R^b$ in formula (2) above.

In formula (c) above, m is an integer of 1 to 10, preferably 1 to 5, more preferably 1 to 3, and even more preferably 1.

In one embodiment of the present invention, $L^A$ in general formula (2) above is preferably a linking group represented by any one of formulae (a) to (d) above.

In particular, when x1 and x2 in general formula (2) above are 0, $L^A$ is preferably a linking group represented by formula (a), formula (c) or formula (d) above, more preferably a linking group represented by formula (a) above, and even more preferably a linking group represented by formula (a) above, wherein $R^c$ and $R^d$ are a methyl group.

Further, when x1 and x2 in general formula (2) above are not 0, $L^A$ is preferably a linking group represented by formula (b) above.

Examples of the structural unit (2) include structural units derived from 4,4-bis(4-hydroxyphenyl)propane (i.e., bisphenol A; BPA), 2,2-bis(4-hydroxy-3-methylphenyl)propane (i.e., bisphenol C; BPC), 4,4'-biphenyldiol, bis(4-hydroxyphenyl)methane, bis(2-hydroxyphenyl)methane, 2,4'-dihydroxydiphenylmethane, bis(4-hydroxyphenyl)ether, bis(4-hydroxyphenyl) sulfone, 2,4'-dihydroxydiphenyl sulfone, bis(2-hydroxyphenyl) sulfone, bis(4-hydroxy-3-methylphenyl) sulfone, bis(4-hydroxyphenyl) sulfoxide, bis(4-hydroxyphenyl) sulfide, bis(4-hydroxyphenyl) ketone, 1,1-bis (4-hydroxyphenyl)ethane, 1,1-bis(4-hydroxyphenyl)-1-phenylethane, bis(4-hydroxyphenyl)diphenylmethane, 2,2-bis(4-hydroxyphenyl)propane, 1,1-bis(4-hydroxy-3-methylphenyl)ethane, bis(4-hydroxy-3-methylphenyl)methane, 2,2-bis(4-hydroxy-3-t-butylphenyl)propane, 2,2-bis(4-hydroxyphenyl)butane, 1,1-bis(4-hydroxyphenyl)cyclohexane, 1,1-bis(4-hydroxy-3-methylphenyl)cyclohexane, 1,1-bis(4-hydroxyphenyl)cycloundecane, 1,1-bis(4-hydroxyphenyl)cyclododecane, 2,2-bis(4-hydroxy-3-allylphenyl)propane, 2,2-bis(4-hydroxyphenyl)butane, 1,1-bis(4-hydroxyphenyl)-2-ethylhexane, 1,1-bis(4-hydroxyphenyl)-2-methylpropane, 2,2-bis(4-hydroxyphenyl)-4-methylpentane, 1,1-bis(4-hydroxyphenyl)decane, 1,3-bis(4-hydroxyphenyl)-5,7-dimethyladamantane, 2,2-bis(4-(2-hydroxyethoxy)phenyl)propane, 4,4-bis(2-hydroxyethoxy)biphenyl, 2,2'-(1,4-phenylene)bis(ethan-1-ol), 2,2'-(1,4-phenylene)bis(methan-1-ol), 2,2'-(1,4-phenylenebis(oxy))bis(ethan-1-ol), 1,1-bis(4-hydroxyphenyl)cyclododecane, 1,1-bis(4-hydroxy-3-methylphenyl)cyclododecane, 1,1-bis(4-hydroxy-3-phenylphenyl)cyclododecane, 1,1-bis(4-hydroxy-3-t-butylphenyl)cyclododecane, 1,1-bis(4-hydroxy-3-sec-butylphenyl)cyclododecane, 1,1-bis(4-hydroxy-3-allylphenyl)cyclododecane, 1,1-bis(4-hydroxy-3,5-dimethylphenyl)cyclododecane, 1,1-bis(4-hydroxy-3-fluorophenyl)cyclododecane, 1,1-bis(4-hydroxy-3-chlorophenyl)cyclododecane, 1-bis(4-hydroxy-3-bromophenyl)cyclododecane, 7-ethyl-1,1-bis(4-hydroxyphenyl)cyclododecane, 3,6-dimethyl-1,1-bis(4-hydroxyphenyl)cyclododecane, 9,9-bis(4-(2-hydroxyethoxy)phenyl)fluorene, 9,9-bis(4-(2-hydroxyethoxy)-3-methylphenyl)fluorene, 9,9-bis(4-(2-hydroxyethoxy)-3-tert-butylphenyl)fluorene, 9,9-bis(4-(2-hydroxyethoxy)-3-isopropylphenyl)fluorene, 9,9-bis(4-(2-hydroxyethoxy)-3-cyclohexylphenyl)fluorene, 9,9-bis(4-(2-hydroxyethoxy)-3-phenylphenyl)fluorene or the like.

Among them, structural units derived from 4,4-bis(4-hydroxyphenyl)propane (BPA), 2,2-bis(4-hydroxy-3-methylphenyl)propane (BPC), 1,1-bis(4-hydroxyphenyl)cyclohexane or 1,1-bis(4-hydroxyphenyl)ethane are preferred, and structural units derived from 4,4-bis(4-hydroxyphenyl)propane (BPA) or 2,2-bis(4-hydroxy-3-methylphenyl)propane (BPC) are more preferred. A structural unit derived from 4,4-bis(4-hydroxyphenyl)propane (BPA) is particularly preferred because it has broad utility, can be easily obtained at a low price as a high-quality monomer in which impurities such as a metal component are not mixed, and has excellent heat resistance.

In the polycarbonate resin, as the structural unit (2), one type may be used solely, or two or more types may be used in combination.

In one embodiment, the polycarbonate resin is a copolymer which comprises the structural unit (1) including a structural unit represented by formula 9 below and the structural unit (2). In one embodiment, the polycarbonate resin is a copolymer which comprises a structural unit represented by formula 9 below and the structural unit (2).

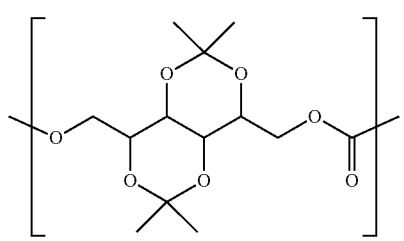

9

In one embodiment, the polycarbonate resin is a copolymer which comprises the structural unit (1) including a structural unit represented by formula 4 below and the structural unit (2). In one embodiment, the polycarbonate resin is a copolymer which comprises a structural unit represented by formula 4 below and the structural unit (2).

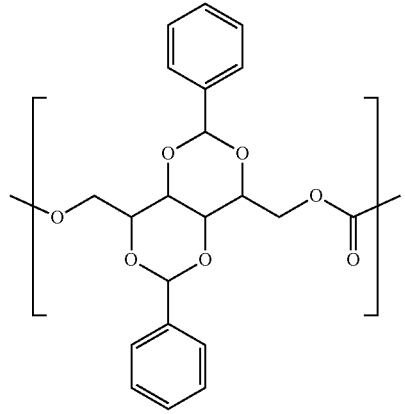

4

In one embodiment, the polycarbonate resin is a copolymer which comprises the structural unit (1) including a structural unit represented by formula 1 below and the structural unit (2). In one embodiment, the polycarbonate resin is a copolymer which comprises a structural unit represented by formula 1 below and the structural unit (2).

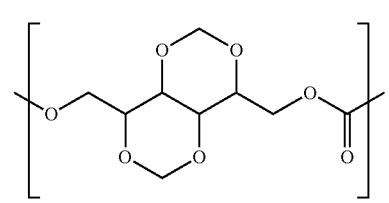

1

The content of the structural unit (1) in the polycarbonate resin is preferably 0.01 mol % or more, more preferably 0.1 mol % or more, even more preferably 1 mol % or more, still more preferably 10 mol % or more, and particularly preferably 30 mol % or more, while it is preferably 100 mol % or less, more preferably 99 mol % or less, even more preferably 90 mol % or less, still more preferably 70 mol % or less, and particularly preferably 60 mol % or less relative to the total amount (100 mol %) of structural units of the polycarbonate resin.

The content of the structural unit (2) in the polycarbonate resin is preferably 0.01 mol % or more, more preferably 0.1 mol % or more, even more preferably 1 mol % or more, still more preferably 10 mol % or more, and particularly preferably 30 mol % or more, while it is preferably 100 mol % or less, more preferably 99 mol % or less, even more preferably 90 mol % or less, still more preferably 80 mol % or less, and particularly preferably 70 mol % or less relative to the total amount (100 mol %) of structural units of the polycarbonate resin.

The polycarbonate resin may have another structural unit other than the structural unit (1) and the structural unit (2).

Note that the total content of the structural unit (1) and the structural unit (2) is preferably 70 to 100 mol %, more preferably 80 to 100 mol %, even more preferably 90 to 100 mol %, still more preferably 95 to 100 mol %, and particularly preferably 100 mol % relative to the total amount (100 mol %) of structural units of the polycarbonate resin.

The content of said another structural unit is preferably 0 to 30 mol %, more preferably 0 to 30 mol %, even more preferably 0 to 10 mol %, still more preferably 0 to 5 mol %, and particularly preferably 0 mol % relative to the total amount (100 mol %) of structural units of the polycarbonate resin.

Examples of said another structural unit include structural units derived from 1,3-adamantanediol, pentacyclopentadecanedimethanol, 1,4-cyclohexanedimethanol, 1,3-adamantanedimethanol, decalin-2,6-dimethanol, tricyclodecanedimethanol, fluorene glycol, fluorene diethanol or isosorbide.

In the polycarbonate resin, the content ratio between the structural unit (1) and the structural unit (2) [(1)/(2)] (molar ratio) is preferably 0.01/99.99 to 99.99/0.01. From the viewpoint of moldability, the content ratio between the structural unit (1) and the structural unit (2) [(1)/(2)] is more preferably 1/99 to 99/1, even more preferably 10/90 to 90/10, still more preferably 20/80 to 80/20, and particularly preferably 30/70 to 60/40.

The weight average molecular weight (Mw) of the polycarbonate resin is not particularly limited, but from the viewpoint of moldability, it is preferably 10,000 to 70,000, more preferably 10,000 to 50,000, and even more preferably 20,000 to 50,000.

The molecular weight distribution (Mw/Mn) of the polycarbonate resin is preferably 5.0 or less, more preferably 3.5 or less, even more preferably 3.0 or less, still more preferably 2.5 or less, and particularly preferably 2.0 or less.

In this specification, the weight average molecular weight (Mw) and the number average molecular weight (Mn) are standard polystyrene equivalent values measured by gel permeation chromatography (GPC) and specifically mean values measured by the method described in the Examples. Further, the molecular weight distribution means the ratio between the weight average molecular weight (Mw) and the number average molecular weight (Mn) [Mw/Mn].

The glass transition temperature (Tg) of the polycarbonate resin is preferably 80 to 250° C., more preferably 80 to 150° C., even more preferably 80 to 140° C., still more preferably 100 to 140° C., and particularly preferably 110 to 130° C.

In this specification, the glass transition temperature (Tg) is a value measured by using a differential scanning calorimeter (DSC) and specifically means a value measured by the method described in the Examples.

The thermal decomposition temperature at the time of 5% weight reduction (5% weight reduction temperature) of the polycarbonate resin is preferably 325° C. or higher, more preferably 350° C. or higher, and even more preferably 370° C. or higher. In this specification, the thermal decomposition temperature at the time of 5% weight reduction (5% weight reduction temperature) is a value measured by using an apparatus for simultaneous thermogravimetry/differential thermal analysis (TG/TDA) and specifically means a value measured by the method described in the Examples.

Method for Producing Polycarbonate Resin

The method for producing the polycarbonate resin is not particularly limited, but it is preferably a method having a step of performing a transesterification reaction. In this step, a transesterification reaction between a diol component as a raw material monomer and a carbonic acid diester is performed, thereby obtaining the above-described polycarbonate resin.

As the diol component as the raw material monomer, at least a compound (1)' represented by general formula (1)' below is included.

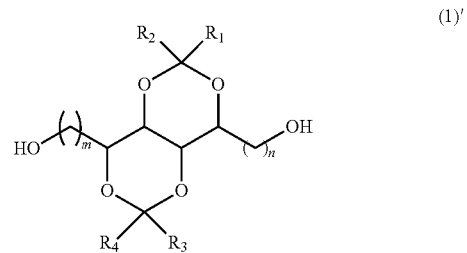

(1)'

In general formula (1)' above, $R_1$, $R_2$, $R_3$, $R_4$, m and n are the same as those in the aforementioned definitions with respect to general formula (1), and preferred embodiments thereof are also the same as described above.

In one embodiment, the compound (1)' is a compound represented by general formula (1a)' below.

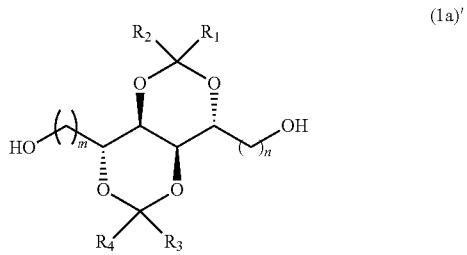

(1a)'

In one embodiment, the compound (1)' is a compound represented by general formula (1b)' below.

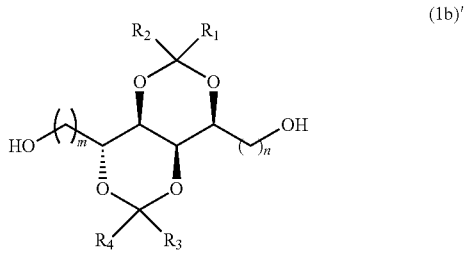

(1b)'

In general formulae (1a)' and (1b)' above, $R_1$, $R_2$, $R_3$, $R_4$, m and n are the same as those in the aforementioned definitions with respect to general formula (1), and preferred embodiments thereof are also the same as described above.

The diol component as the raw material monomer may further include a compound (2)' represented by general formula (2)' below, and according to need, another diol compound.

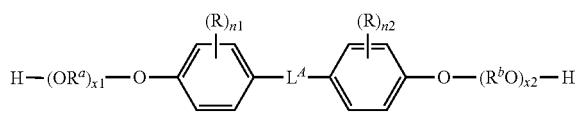

(2)'

In general formula (2)' above, Ra, Rb, R, x1, x2, n1, n2 and $L^A$ are the same as those in the aforementioned definitions with respect to general formula (2), and preferred embodiments thereof are also the same as described above.

The compound (1)' becomes a part of the structure of the structural unit (1), and the compound (2)' becomes a part of the structure of the structural unit (2).

The content of the compound (1)' is preferably 0.01 mol % or more, more preferably 0.1 mol % or more, even more preferably 1 mol % or more, still more preferably 10 mol % or more, and particularly preferably 30 mol % or more, while it is preferably 100 mol % or less, more preferably 99 mol % or less, even more preferably 90 mol % or less, still more preferably 70 mol % or less, and particularly preferably 60 mol % or less relative to the total amount (100 mol %) of the diol component as the raw material monomer.

The content of the compound (2)' is preferably 0.01 mol % or more, more preferably 0.1 mol % or more, even more preferably 1 mol % or more, still more preferably 10 mol % or more, and particularly preferably 30 mol % or more, while it is preferably 100 mol % or less, more preferably 99 mol % or less, even more preferably 90 mol % or less, still more preferably 80 mol % or less, and particularly preferably 70 mol % or less relative to the total amount (100 mol %) of the diol component as the raw material monomer.

The total content of the compound (1)' and the compound (2)' is preferably 70 to 100 mol %, more preferably 80 to 100 mol %, even more preferably 90 to 100 mol %, still more preferably 95 to 100 mol %, and particularly preferably 100 mol % relative to the total amount (100 mol %) of the diol component as the raw material monomer.

The blending ratio between the compound (1)' and the compound (2)' [(1)'/(2)'] (molar ratio) is preferably 0.01/99.99 to 99.99/0.01, more preferably 1/99 to 99/1, even more preferably 10/90 to 90/10, still more preferably 20/80 to 80/20, and particularly preferably 30/70 to 60/40.

Examples of the carbonic acid diester include diphenyl carbonate (DPC), ditolyl carbonate, bis(chlorophenyl) carbonate, m-cresyl carbonate, dimethyl carbonate, diethyl carbonate, dibutyl carbonate and dicyclohexyl carbonate. Among them, from the viewpoint of reduction of a by-product alcohol-based compound which will be described later, a diaryl carbonate compound (e.g., diphenyl carbonate, ditolyl carbonate, bis(chlorophenyl) carbonate, m-cresyl carbonate, etc.) is preferred, and from the viewpoint of reactivity and purity, diphenyl carbonate is more preferred. When a dialkyl carbonate is used as the carbonic acid diester, the remaining amount of a by-produced alkyl alcohol-based compound tends to be larger.

These carbonic acid diesters may be used solely, or two or more of them may be used in combination.

The blending amount of the carbonic acid diester is preferably 1.00 to 1.30 mol, more preferably 1.00 to 1.20 mol, and even more preferably 1.00 to 1.10 mol relative to 1 mol of the diol component (total).

In the transesterification reaction, a transesterification catalyst is preferably used.

Examples of the transesterification catalyst include an organic acid salt, a carbonate, an oxide, a hydroxide, a hydride, an alkoxide or the like of a metal selected from an alkali metal and an alkaline earth metal, and zinc acetate, zinc benzoate, zinc 2-ethylhexanoate, tin(II) chloride, tin (IV) chloride, tin(II) acetate, tin(IV) acetate, dibutyltin dilaurate, dibutyltin oxide, dibutyltin dimethoxide, zirconium acetylacetonato, zirconium oxyacetate, zirconium tetrabutoxide, lead(II) acetate, lead(IV) acetate, zirconium acetate, titanium tetrabutoxide and cesium carbonate.

These transesterification catalysts may be used solely, or two or more of them may be used in combination.

The amount of the transesterification catalyst to be used is preferably $1 \times 10^{-9}$ to $1 \times 10^{-3}$ mol, and more preferably $1 \times 10^{-7}$ to $1 \times 10^{-4}$ mol relative to 1 mol of the diol component.

Regarding specific reaction conditions for the transesterification reaction, it is preferred that the reaction is performed at a reaction temperature of 120 to 260° C. (preferably 180 to 260° C.) for a reaction time of 0.1 to 5 hours (preferably 0.5 to 3 hours).

Next, the pressure reducing degree of the reaction system is increased while increasing the reaction temperature to react the diol compound with another monomer, and it is preferred that a polycondensation reaction is performed finally under a reduced pressure of 300 kPa or less (more preferably 100 kPa or less, and even more preferably 10 kPa or less) (final pressure reducing degree) at 200 to 350° C. for 0.05 to 2 hours. Moreover, from the viewpoint of reduction of an alcohol-based compound such as a phenolic compound which will be described later, it is particularly preferred that a polycondensation reaction is performed finally under a reduced pressure of 1 kPa or less (final pressure reducing degree) at 260 to 350° C. for 0.05 to 2 hours.

In one embodiment, the transesterification reaction is performed under a reduced pressure of 1 kPa or less (final pressure reducing degree) and at a temperature of 260° C. or higher (preferably 260 to 350° C.).

The transesterification reaction may be either a continuous type or a batch type.

The reaction apparatus to be used for performing the above-described reaction may be a vertical apparatus equipped with an anchor type stirring blade, maxblend stirring blade, helicalribbon type stirring blade or the like, or a horizontal apparatus equipped with a paddle blade, lattice blade, spectacle-shaped blade or the like, or an extruder-type apparatus equipped with a screw. Further, in consideration of the viscosity of a polymerized product, use of these reaction apparatuses in suitable combination is preferably carried out.

In the method for producing the polycarbonate resin of one embodiment of the present invention, from the viewpoint of maintaining thermal stability and hydrolytic stability, after the polymerization reaction is completed, the catalyst may be removed or deactivated.

Further, after the catalyst is deactivated, in order to remove a low boiling point compound in the resin, a process of devolatilizing and removing the compound under a pressure of 0.01 to 1 mmHg and at a temperature of 200 to 350° C. may be carried out. In this process, a horizontal apparatus equipped with a stirring blade having excellent surface renewal ability such as a paddle blade, a lattice blade and a spectacle-shaped blade, or a thin film evaporator is suitably used.

It is desired that the content of foreign materials in the resin obtained in this way is as low as possible, and for this reason, filtration of a melting raw material and filtration of a catalyst solution may be carried out. The mesh of the filter to be used for filtration is preferably 5 μm or less, and more preferably 1 μm or less.

The polycarbonate resin obtained in this step may be formed into flakes and used to prepare a polycarbonate resin composition.

Further, according to need, after the polycarbonate resin is isolated based on a well-known method, a pellet of a polycarbonate resin composition may be obtained, for example, by a well-known strand-type cold cut process (a method in which a melted polycarbonate resin composition is molded into a strand shape, cooled, and then it is cut into a predetermined shape for pelletization), an in-air hot-cut process (a method in which a melted polycarbonate resin composition is cut into a pellet shape in air before it contacts with water), or an in-water hot-cut process (a method in which a melted polycarbonate resin composition is cut and cooled at the same time in water for pelletization).

The obtained pellet of the polycarbonate resin composition is preferably dried according to, for example, a drying method using a hot air drying oven, a vacuum drying oven or a dehumidification drying oven according to need.

In the polycarbonate resin obtained in this way, an alcohol-based compound such as a phenolic compound that may be produced as a by-product at the time of the production and a diol component or carbonic acid diester that is unreacted and remains may be present as impurities.

The alcohol-based compound such as the phenolic compound and carbonic acid diester as impurities may cause reduction in the strength of a molded body and odor generation, and for this reason, it is preferred that the contents thereof are as low as possible.

The content of a remaining phenolic compound is preferably 3000 mass ppm or less, more preferably 2000 mass ppm or less, even more preferably 1000 mass ppm or less, still more preferably 800 mass ppm or less, still even more preferably 500 mass ppm or less, and particularly preferably 300 mass ppm or less relative to 100% by mass of the polycarbonate resin.

The content of a remaining diol component is preferably 1000 mass ppm or less, more preferably 500 mass ppm or less, even more preferably 100 mass ppm or less, and still more preferably 10 mass ppm or less relative to 100% by mass of the polycarbonate resin.

The content of a remaining carbonic acid diester is preferably 1000 mass ppm or less, more preferably 500 mass ppm or less, even more preferably 100 mass ppm or less, and still more preferably 10 mass ppm or less relative to 100% by mass of the polycarbonate resin.

It is particularly preferred that the contents of compounds including phenol and t-butylphenol are low, and the contents of these compounds are preferably within the above-described ranges.

The content of the remaining phenolic compound in the polycarbonate resin can be measured according to a technique in which the phenolic compound extracted from the polycarbonate resin is analyzed using gas chromatography.

Similarly, the content of the remaining alcohol-based compound in the polycarbonate resin can be measured according to a technique in which the alcohol-based compound extracted from the polycarbonate resin is analyzed using gas chromatography.

Similarly, the contents of the remaining diol component and carbonic acid diester in the polycarbonate resin can be measured according to a technique in which these compounds are extracted from the polycarbonate resin and analyzed using gas chromatography.

The contents of the by-product alcohol-based compound such as the phenolic compound, the diol component and carbonic acid diester may be reduced to an undetectable level, but from the viewpoint of the productivity, slight amounts of these substances may be comprised within a range in which effects are not reduced. Further, when slight amounts of these substances are comprised, satisfactory plasticity can be obtained at the time of melting the resin.

The content of each of the remaining phenolic compound, diol component and carbonic acid diester maybe, for example, 0.01 mass ppm or more, 0.1 mass ppm or more, or 1 mass ppm or more relative to 100% by mass of the polycarbonate resin.

The content of the remaining alcohol-based compound maybe, for example, 0.01 mass ppm or more, 0.1 mass ppm or more, or 1 mass ppm or more relative to 100% by mass of the polycarbonate resin.

Note that the contents of the by-product alcohol-based compound such as the phenolic compound, the diol component and carbonic acid diester in the polycarbonate resin can be adjusted to be within the above-described ranges by suitably adjusting conditions for polycondensation and settings of apparatuses. The adjustment can also be carried out by changing conditions for the extrusion process after polycondensation.

For example, the remaining amount of the by-product alcohol-based compound such as the phenolic compound is associated with the type of the carbonic acid diester to be used for the polymerization of the polycarbonate resin, the polymerization reaction temperature, the polymerization pressure, etc. By changing these conditions, the remaining amount of the by-product alcohol-based compound such as the phenolic compound can be reduced.

For example, when a polycarbonate resin is produced using a dialkyl carbonate such as a diethyl carbonate, the molecular weight is not easily increased, resulting in a low-molecular-weight polycarbonate, and the content of a by-produced alkyl alcohol-based compound tends to be higher. Such an alkyl alcohol has high volatility, and when it is remained in the polycarbonate resin, moldability of the resin tends to be deteriorated. Further, when the remaining amount of the by-product alcohol-based compound such as the phenolic compound is large, a problem of odor may be caused at the time of molding the resin, and a cleavage reaction of a resin skeleton may proceed at the time of compounding, resulting in reduction in the molecular weight. Accordingly, it is preferred that the content of the remaining by-product alcohol-based compound in the obtained polycarbonate resin is 3000 mass ppm or less relative to the polycarbonate resin (100% by mass). The content of the remaining alcohol-based compound is preferably 3000 mass ppm or less, more preferably 2000 mass ppm or less, even more preferably 1000 mass ppm or less, still more preferably 800 mass ppm or less, still even more preferably 500 mass ppm or less, and particularly preferably 300 mass ppm or less relative to 100% by mass of the polycarbonate resin.

Monomer Compound

One embodiment of the present invention relates to a monomer compound which enables the achievement of the above-described polycarbonate resin.

One embodiment is a compound represented by general formula (1)':

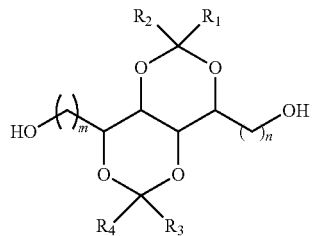
(1)'

In one embodiment, the compound (1)' is a compound represented by general formula (1a)':

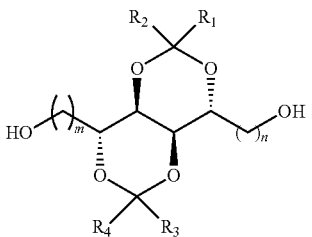
(1a)'

In one embodiment, the compound (1)' is a compound represented by general formula (1b)':

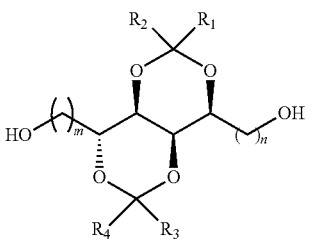
(1b)'

In general formulae (1)', (1a)' and (1b)' above, $R_1$, $R_2$, $R_3$, $R_4$, m and n are the same as those in the aforementioned definitions with respect to general formula (1), and preferred embodiments thereof are also the same as described above.

In one embodiment, in formulae (1)', (1a)' and (1b)' above, there is no case where all of $R_1$, $R_2$, $R_3$ and $R_4$ are a hydrogen atom.

Polycarbonate Resin Composition

One embodiment of the present invention relates to a polycarbonate resin composition (hereinafter also referred to as just "resin composition") which comprises the polycarbonate resin of the above-described embodiment.

In the resin composition, the content of the polycarbonate resin of the above-described embodiment is usually 30 to 100% by mass, preferably 50 to 100% by mass, more preferably 60 to 100% by mass, even preferably 70 to 100% by mass, and still more preferably 80 to 100% by mass relative to the total amount (100% by mass) of the resin composition.

The resin composition may comprise another resin other than the polycarbonate resin of the above-described embodiment.

Examples of said another resin include: a thermoplastic polyester resin such as a polycarbonate resin other than the polycarbonate resin of the above-described embodiment, a polyethylene terephthalate resin (PET resin), a polytrimethylene terephthalate resin (PTT resin) and a polybutyrene terephthalate resin (PBT resin); a styrene-based resin such as a polystyrene resin (PS resin), a high impact polystyrene resin (HIPS), an acrylonitrile-styrene copolymer (AS resin) and a methyl methacrylate-styrene copolymer (MS resin); an elastomer such as a core/shell type elastomer including a methyl methacrylate-acrylic rubber-styrene copolymer (MAS) and a polyester-based elastomer; a polyolefin resin such as a cyclic cycloolefin resin (COP resin) and a cyclic cycloolefin (COP) copolymer resin; a polyamide resin (PA resin); a polyimide resin (PI resin); a polyetherimide resin (PEI resin); a polyurethane resin (PU resin); a polyphenylene ether resin (PPE resin); a polyphenylene sulfide resin (PPS resin); a polysulfone resin (PSU resin); a polymethacrylate resin (PMMA resin); and polycaprolactone.

As said another resin, these resins may be comprised solely, or two or more of them may be comprised as a mixture.

In the resin composition, the content of said another resin is not particularly limited as long as it is within a range in which effects of the present invention are not reduced, but for example, it is preferably 0 to 50 parts by mass, more preferably 0 to 20 parts by mass, even more preferably 0 to 10 parts by mass, still more preferably 0 to 5 parts by mass, and particularly preferably 0 to 1 part by mass relative to the total amount (100 parts by mass) of the polycarbonate resin of the present invention to be comprised in the resin composition.

The resin composition may comprise various additives within ranges in which effects of the present invention are not reduced.

Such various additives are suitably selected according to intended use. For example, a thermal stabilizer, an antioxidant, a flame retardant, a flame retardant auxiliary agent, an ultraviolet absorber, a mold release agent, a coloring agent, etc. are preferably comprised, and according to need, an antistatic agent, a fluorescent brightener, an antifog additive, a flowability improving agent, a plasticizer, a dispersing agent, an antimicrobial agent, etc. may also be comprised.

Molded Body

Another embodiment of the present invention relates to a molded body obtained by molding the polycarbonate resin composition.

The molding method is not particularly limited, and molding is carried out according to any method, for example, the injection molding method, the high-speed injection molding method, the injection compression molding method, the two-color molding method, the blow molding method such as gas-assisted molding, a molding method using a heat insulating mold, a molding method using a rapid heating mold, foam molding (including supercritical fluid), insert molding, the IMC (in-mold coating) molding method, the extrusion molding method, the sheet molding method, the thermoforming method, the rotational molding method, the laminate molding method, the press molding method, the compression molding method, the extrusion molding method, the solution casting method or the like. Further, it is also possible to use a molding method using the hot runner system.

The shape, pattern, color, size, etc. of the molded body can be suitably selected according to the intended use of the molded body. The resin or molded body may be subjected to a surface treatment such as hard coating and antireflection treatment according to need.

Examples of the molded body include electrical and electronic equipments, OA (office automation) equipments, information terminal devices, machine components, home appliances, vehicle components, building components, various containers, leisure goods/sundries, components for lighting equipments, components for various household electric appliances, housings, containers, covers, storage parts and cases of electrical appliances, and covers and cases of lighting equipments.

Examples of the electrical and electronic equipments include personal computers, game machines, television receivers, display units such as liquid crystal display devices and plasma display devices, printers, copy machines, scanners, facsimiles, electronic organizers, personal digital assistants (PDAs), electronic desk calculators, electronic dictionaries, cameras, video cameras, mobile telephones, battery packs, drives and readers of storage media, mouse devices, numeric keypads, various music players and portable radio sets/audio players.

Further, examples of the molded body also include illuminated billboards, liquid crystal backlights, lighting displays, traffic signs, signboards, screens, automobile components such as reflectors and meter parts, toys and ornaments.

In particular, the molded body can be preferably used as cases and interior and exterior materials of electronic equipments, automobiles, etc. because the molded body has excellent heat resistance.

EXAMPLES

Hereinafter, the present invention will be described in more detail by way of examples. However, the present invention is not limited to the below-described examples, and can be arbitrarily changed and then carried out without departing from the gist of the present invention.

In this specification, "room temperature", "normal temperature" or "rt" usually means about 10° C. to about 35° C. "%" means "% by weight" unless otherwise specified.

The measurement of respective physical properties of the resins obtained in synthesis examples, working examples and comparative examples was carried out according to procedures described below.

Evaluation

1. Weight Average Molecular Weight (Mw), Number Average Molecular Weight (Mn) and Molecular Weight Distribution (Mw/Mn)

Using gel permeation chromatography (GPC) and chloroform as a developing solvent, a calibration curve was produced using a standard polystyrene having an already-known molecular weight (molecular weight distribution=1) (PStQuick MP-M manufactured by Tosoh Corporation). The elution time and molecular weight value of each peak were plotted based on the measured standard polystyrene, and three-dimensional approximation was conducted to obtain a calibration curve.

Measurement Conditions

Apparatus: HLC-8320GPC manufactured by Tosoh Corporation
Columns:
  Guard column: TSKguardcolumn SuperMPHZ-M×1
  Analysis column: TSKgel SuperMultiporeHZ-M×3
Solvent: HPLC grade chloroform
Injection amount: 10 μL
Sample concentration: 0.2 w/v % HPLC grade chloroform solution
Flow rate of solvent: 0.35 ml/min
Measurement temperature: 40° C.
Detector: RI Based on the obtained calibration curve, the weight average molecular weight (Mw) and the number average molecular weight (Mn) were obtained as polystyrene equivalent values using the below-described calculation formulae. Further, from the polystyrene equivalent weight average molecular weight (Mw) and the polystyrene equivalent number average molecular weight (Mn), the molecular weight distribution (Mw/Mn) was obtained using the below-described calculation formula.

$$Mw=\Sigma(Wi \times Mi) \div \Sigma(Wi)$$

$$Mn=\Sigma(Ni \times Mi) \div \Sigma(Ni)$$

Molecular weight distribution=$Mw/Mn$ [Calculation formulae]

(In the above-described formulae, "i" represents the "i"th dividing point when dividing the molecular weight M, "Wi" represents the "i"th weight, "Ni" represents the "i"th number of molecules, and "Mi" represents the "i"th molecular weight. The molecular weight M represents the value of the molecular weight of polystyrene at the corresponding elution time in the calibration curve.)

2. Glass Transition Temperature (Tg)

The glass transition temperature (Tg) was measured using a differential scanning calorimeter (DSC) (manufactured by Hitachi High-Tech Science Corporation, DSC-7000).

7 to 12 mg of a test piece was precisely weighed in an RDC aluminum pan (sample container for AI autosampler, φ 6.8, H 2.5 mm), and it was sealed using a cover for AI autosampler, thereby preparing a measurement sample.

The measurement was carried out under nitrogen atmosphere (flow rate of nitrogen: 50 ml/min). For a reference cell, 10.0 mg of sapphire was used as a reference substance. The sample temperature was adjusted to 30° C., and then it was increased to 220° C. at a rate of 10° C./min. After that, cooling was carried out to decrease the temperature to 30° C. at a rate of 10° C./min. After that, the temperature was increased to 270° C. at a rate of 10° C./min, and the measurement was carried out.

3. Thermal Decomposition Temperature (5% Weight Reduction Temperature)

The thermal decomposition temperature (5% weight reduction temperature) was measured using an apparatus for simultaneous thermogravimetry/differential thermal analysis (TG/DTA) (TGDTA7300 manufactured by Hitachi High-Tech Science Corporation).

2 mg of a test piece was precisely weighed in a platinum pan (Pt open type sample container, φ5.2, H 2.5 mm) to prepare a measurement sample.

The measurement was carried out under nitrogen atmosphere (flow rate of nitrogen: 250 ml/min). For a reference cell, 0.00519 g of α-alumina was used as a reference substance. The sample temperature was adjusted to 30° C. and then increased to 550° C. at a rate of 10° C./min, and then the measurement was carried out.

Example 1

2:4-3:5-di-O-methylene-D-mannitol (DMAN-DOM) (7.48 g, 36.28 mmol), BPA (17.52 g, 76.74 mmol) and DPC (24.94 g, 116.4 mmol) as raw material monomers, and cesium carbonate ($CsCO_3$, $2 \times 10^{-6}$ mol relative to the total (1 mol) of DMAD-DOM and BPA) as a catalyst were precisely weighed in a 100 mL four-neck flask, and drying under reduced pressure was carried out at normal temperature and under vacuum for 1 hour. After that, substitution with nitrogen was carried out 3 times so that the reaction system was under nitrogen atmosphere.

A stirring machine and a distillation apparatus were attached to the four-neck flask, and it was heated to 180° C. under nitrogen atmosphere (pressure: 101.3 kPa). After heating, complete dissolution of the raw material monomers was confirmed, and after that, the temperature was elevated to 200° C. at a rate of 120° C./h, and simultaneously, the pressure in the reactor was reduced to 27 kPa, and stirring was carried out for 40 minutes. After that, the temperature was elevated to 210° C. at a rate of 60° C./h. After that, the degree of pressure reduction was adjusted to 24 kPa, and stirring was carried out for 10 minutes. After that, the temperature was elevated to 220° C. at a rate of 60° C./h. After that, the temperature was elevated to 230° C. at a rate of 60° C./h. After that, the degree of pressure reduction was adjusted to 20 kPa, and stirring was carried out for 10 minutes. After that, the temperature was elevated to 240° C. at a rate of 60° C./h, and simultaneously, the degree of pressure reduction was adjusted to 14 Pa, and stirring was carried out for 10 minutes. After that, the temperature was elevated to 250° C. at a rate of 60° C./h, and simultaneously, the degree of pressure reduction was adjusted to 7 Pa, and stirring was carried out for 10 minutes. After that, the temperature was elevated to 260° C. at a rate of 60° C./h. After that, the temperature was elevated to 270° C. at a rate of 60° C./h. After that, the degree of pressure reduction was adjusted to 1 kPa or less, and stirring was further carried out for 120 minutes, and the reaction was completed. After the reaction was completed, nitrogen was introduced into the reactor to obtain ordinary pressure, and a polycarbonate resin produced was taken out therefrom.

The obtained polycarbonate resin was transparent.

Example 2

A polycarbonate resin was obtained in a manner similar to that in Example 1, except that 2:4-3:5-di-O-methylene-D-mannitol (DMAN-DOM) (7.48 g, 36.28 mmol), bisphenol A (BPA) (17.52 g, 76.74 mmol) and diphenyl carbonate (DPC) (25.42 g, 118.66 mmol) were used as raw material monomers.

The obtained polycarbonate resin was transparent.

Example 3

2:4-3:5-di-O-methylene-D-mannitol (DMAN-DOM) (12.51 g, 60.67 mmol), BPA (54.71 g, 76.74 mmol) and DPC (26.20 g, 122.30 mmol) as raw material monomers, and cesium carbonate ($CsCO_3$, $2 \times 10^{-6}$ mol relative to the total (1 mol) of DMAD-DOM and BPA) as a catalyst were precisely weighed in a 100 mL four-neck flask, and drying under reduced pressure was carried out at normal temperature and under vacuum for 1 hour. After that, substitution with nitrogen was carried out 3 times so that the reaction system was under nitrogen atmosphere.

A stirring machine and a distillation apparatus were attached to the four-neck flask, and it was heated to 180° C. under nitrogen atmosphere (pressure: 101.3 kPa). After heating, complete dissolution of the raw material monomers was confirmed, and after that, the temperature was elevated to 200° C. at a rate of 120° C./h, and simultaneously, the pressure in the reactor was reduced to 27 kPa, and stirring was carried out for 50 minutes. After that, the temperature was elevated to 210° C. at a rate of 60° C./h. After that, the degree of pressure reduction was adjusted to 24 kPa, and stirring was carried out for 10 minutes. After that, the temperature was elevated to 220° C. at a rate of 60° C./h. After that, the temperature was elevated to 230° C. at a rate of 60° C./h. After that, the degree of pressure reduction was adjusted to 20 kPa, and stirring was carried out for 10 minutes. After that, the temperature was elevated to 240° C. at a rate of 60° C./h. After that, the degree of pressure reduction was adjusted to 14 Pa, and stirring was carried out for 10 minutes. After that, the temperature was elevated to 250° C. at a rate of 60° C./h. After that, the degree of pressure reduction was adjusted to 7 Pa, and stirring was carried out for 10 minutes. After that, the degree of pressure reduction was adjusted to 1 kPa or less, and stirring was further carried out for 120 minutes, and the reaction was completed. After the reaction was completed, nitrogen was introduced into the reactor to obtain ordinary pressure, and a polycarbonate resin produced was taken out therefrom. The obtained polycarbonate resin was transparent.

Example 4

A polycarbonate resin was obtained in a manner similar to that in Example 3, except that 2:4-3:5-di-O-methylene-D-mannitol (DMAN-DOM) (12.51 g, 60.67 mmol) and DPC (13.00 g, 60.67 mmol) as raw material monomers and cesium carbonate ($CsCO_3$, $2 \times 10^{-6}$ mol relative to 1 mol of DMAD-DOM) as a catalyst were used. The obtained polycarbonate resin was transparent.

Comparative Example 1

Cyclohexanedimethanol (CHDM) (25.00 g, 173.4 mmol, a mixture of a cis form and a trans form) and DPC (36.17 g, 168.9 mmol) as raw material monomers and sodium hydrogen carbonate ($NaHCO_3$, $6 \times 10^{-6}$ mol relative to 1 mol of CHDM) as a catalyst were precisely weighed in a 100 mL four-neck flask, and drying under reduced pressure was carried out at normal temperature and under vacuum for 1 hour. After that, substitution with nitrogen was carried out 3 times so that the reaction system was under nitrogen atmosphere.

A stirring machine and a distillation apparatus were attached to the four-neck flask, and it was heated to 180° C. under nitrogen atmosphere (pressure: 101.3 kPa). After heating, complete dissolution of the raw material monomers was confirmed, and after that, the pressure in the reactor was reduced to 20 kPa, and stirring was carried out for 20 minutes. After that, the temperature was elevated to 200° C. at a rate of 60° C./h, and stirring was carried out at 200° C. for 30 minutes. After that, the temperature was elevated to 225° C. at a rate of 60° C./h. After that, the degree of pressure reduction was adjusted to 16 kPa, and stirring was carried out for 10 minutes. After that, the temperature was elevated to 240° C. at a rate of 60° C./h, and simultaneously, the degree of pressure reduction was adjusted to 12 kPa, and stirring was carried out for 10 minutes. After that, the degree of pressure reduction was adjusted to 8 kPa, and stirring was carried out for 10 minutes. After that, the degree of pressure reduction was adjusted to 5.3 kPa, and stirring was carried out for 10 minutes. After that, the degree of pressure reduction was adjusted to 2.7 kPa, and stirring was carried out for 10 minutes. After that, the degree of pressure reduction was adjusted to 1.3 kPa, and stirring was carried out for 10 minutes. After that, the degree of pressure reduction was adjusted to 1 kPa or less, and stirring was further carried out for 60 minutes, and the reaction was completed. After the reaction was completed, nitrogen was introduced into the reactor to obtain ordinary pressure, and a polycarbonate resin produced was taken out therefrom.

The obtained polycarbonate resin was transparent.

Comparative Example 2

A polycarbonate resin was obtained in a manner similar to that in Comparative Example 1, except that isosorbide (ISB) (43.84 g, 300.0 mmol) and DPC (65.16 g, 304.2 mmol) as raw material monomers and sodium hydrogen carbonate (NaHCO$_3$, 4×10$^{-6}$ mol relative to 1 mol of ISB) as a catalyst were used.

The obtained polycarbonate resin was transparent.

Comparative Example 3

30.61 g (0.101 mol) of spiroglycol (SPG), 21.97 g (0.103 mol) of diphenyl carbonate and 0.10 mg (1.2 µmol) of sodium hydrogen carbonate were put into a 300 mL reactor equipped with a stirring machine and a distillation apparatus, and the operation was carried out in a manner similar to that in Example 1 except for the feed amounts to try to obtain a polycarbonate resin. However, crystallization proceeded while polymerization proceeded, and it was impossible to obtain a polymer.

Note that the structures of the monomer compounds and catalysts used in the Examples and Comparative Examples are as follows:

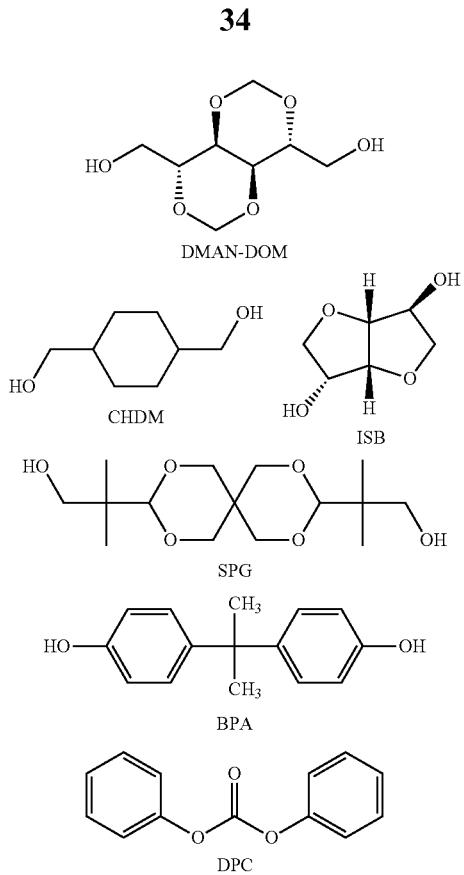

Regarding the polycarbonate resins obtained in the Examples and Comparative Examples, the weight average molecular weight (Mw), the number average molecular weight (Mn), the molecular weight distribution (Mw/Mn), the glass transition temperature (Tg) and the thermal decomposition temperature (5% weight reduction temperature) thereof were measured. The results are shown in Table 1.

TABLE 1

| | Monomer (raw material)/mol % | | | | | Polycarbonate resin | | | | |
|---|---|---|---|---|---|---|---|---|---|---|
| | Compound (1)' | Compound (2)' | Others | | | | | | Tg | 5% weight reduction |
| | DMAN-DOM | BPA | CHDM | ISB | SPG | Mw | Mn | Mw/Mn | (° C.) | temperature (° C.) |
| Example 1 | 32.1 | 67.9 | 0 | 0 | 0 | 31400 | 13400 | 2.34 | 129.4 | 381.9 |
| Example 2 | 32.1 | 67.9 | 0 | 0 | 0 | 27900 | 13900 | 2.01 | 126.6 | 380.4 |
| Example 3 | 52.6 | 47.4 | 0 | 0 | 0 | 23000 | 12300 | 1.87 | 119.0 | 371.8 |
| Example 4 | 100 | 0 | 0 | 0 | 0 | 24000 | 12500 | 1.92 | 85.0 | 350.1 |
| Comparative Example 1 | 0 | 0 | 100 | 0 | 0 | 58700 | 22200 | 2.64 | 46.1 | 323.0 |
| Comparative Example 2 | 0 | 0 | 0 | 100 | 0 | 22100 | 11000 | 2.01 | 117.3 | 318.9 |
| Comparative Example 3 | 0 | 0 | 0 | 0 | 100 | — | — | — | — | — |

It is confirmed from Table 2 above that the polycarbonate resins comprising the structural unit (1) derived from the compound represented by formula (1)' (Examples 1-4) have a high glass transition temperature (Tg) and a high thermal decomposition temperature (5% weight reduction temperature) and have excellent heat resistance.

Meanwhile, in the case of Comparative Example 1 in which the structural unit (1) was not comprised and the structural unit derived from CHDM was comprised, the glass transition temperature (Tg) and the thermal decomposition temperature (5% weight reduction temperature) were low and heat resistance was poor. Further, in the case of Comparative Example 2 in which the structural unit (1) was not comprised and the structural unit derived from ISB was comprised, the thermal decomposition temperature (5% weight reduction temperature) was low. Further, in the case of Comparative Example 3 in which SPG having a skeleton similar to that of the compound represented by formula (1)' was used, the polycarbonate resin was crystallized and it was impossible to observe the glass transition temperature (Tg).

Further, in Examples 1-4, the transparent polycarbonate resins were obtained, but in Comparative Example 3, crystallization occurred at the time of polymerization and it was impossible to sufficiently promote the polymerization. It is inferred that this is because, when using SPG as a monomer, crystallization is caused in the early stage of polymerization due to excessive packing property between polymers and as a result, it is impossible to obtain a high-molecular-weight body.

The scope of the present invention is not limited to the description above. In addition to the above-described examples, the present invention can be suitably changed and then practiced within a range in which the effects of the present invention are not reduced. Note that all the documents and publications cited herein are incorporated herein by reference in their entireties regardless of purposes thereof. In addition, the contents disclosed in the claims and specification of Japanese Patent Application No. 2019-171377 (filed on Sep. 20, 2019), to which priority is claimed by the present application, are incorporated herein.

INDUSTRIAL APPLICABILITY

The polycarbonate resin of the present invention has heat resistance and is useful as a resin which can be produced using a raw material derived from a natural material.

The invention claimed is:

1. A polycarbonate resin which comprises a structural unit (1) represented by general formula (1) and a structural unit (2) represented by general formula (2):

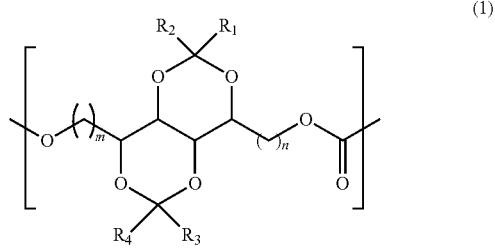

(1)

wherein in general formula (1):
$R_1$, $R_2$, $R_3$ and $R_4$ are each independently selected from the group consisting of a hydrogen atom, an alkyl group having 1 to 10 carbon atoms, an aryl group having 6 to 20 carbon atoms and an alkoxy group having 1 to 10 carbon atoms, and the alkyl group, the aryl group and the alkoxy group of $R_1$, $R_2$, $R_3$ and $R_4$ may be further substituted with a substituent; and m and n each independently represent an integer of 0 to 5,

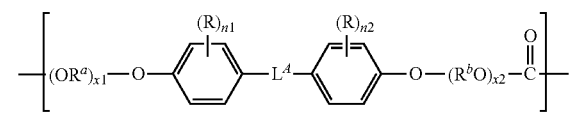

(2)

wherein in general formula (2):
$R^a$ and $R^b$ each independently represent an alkylene group having 1 to 8 carbon atoms;
R each independently represents an alkyl group having 1 to 8 carbon atoms or an aryl group having 6 to 12 carbon atoms;
x1 and x2 each independently represent an integer of 0 to 10;
n1 and n2 each independently represent an integer of 0 to 4; and
$L^A$ represents a single bond or a linking group represented by any one of formulae (a) to (g):

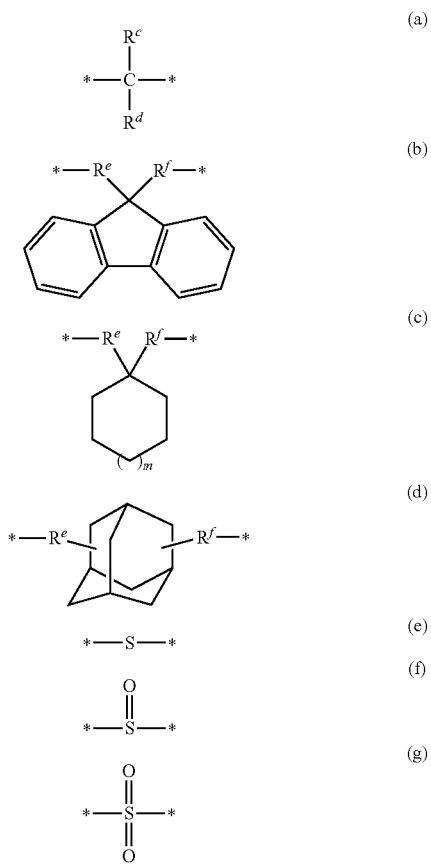

wherein:
* represents a bonding position;
$R^c$ and $R^d$ each independently represent a hydrogen atom, an alkyl group having 1 to 8 carbon atoms or an aryl group having 6 to 12 carbon atoms;
$R^e$ and $R^f$ each independently represent a single bond or an alkylene group having 1 to 4 carbon atoms; and
m' represents an integer of 1 to 10.

2. The polycarbonate resin according to claim 1, wherein the having a molar content ratio between the structural unit (1) and the structural unit (2) [(1)/(2)] of 0.01/99.99 to 99.99/0.01.

3. The polycarbonate resin according to claim 1, wherein the structural unit (2) includes at least one unit derived from a compound selected from the group consisting of 2,2-bis(4-hydroxyphenyl) propane, 2,2-bis(4-hydroxy-3-methylphenyl) propane, 1,1-bis(4-hydroxyphenyl) cyclohexane and 1,1-bis(4-hydroxyphenyl) ethane.

4. The polycarbonate resin according to claim 1, wherein:

$R_1$, $R_2$, $R_3$ and $R_4$ are each independently selected from the group consisting of a hydrogen atom, an alkyl group having 1 to 3 carbon atoms, an aryl group having 6 to 10 carbon atoms and an alkoxy group having 1 to 3 carbon atoms, and the alkyl group, the aryl group and the alkoxy group of $R_1$, $R_2$, $R_3$ and $R_4$ may be further substituted with a substituent; and m and n each independently represent an integer of 1 to 3.

5. The polycarbonate resin according to claim 1, wherein:

both $R_1$ and $R_3$ are a hydrogen atom, $R_2$ and $R_4$ are each independently selected from the group consisting of a hydrogen atom, an alkyl group having 1 to 10 carbon atoms, an aryl group having 6 to 20 carbon atoms and an alkoxy group having 1 to 10 carbon atoms, and the alkyl group, the aryl group and the alkoxy group of $R_2$ and $R_4$ may be further substituted with the substituent; and m and n each independently represent an integer of 0 to 5.

6. The polycarbonate resin according to claim 1, which has a weight average molecular weight (Mw) of 10,000 to 70,000.

7. The polycarbonate resin according to claim 1, having a content of the structural unit (1) in the polycarbonate resin of 30 to 70 mol % and a content of the structural unit (2) in the polycarbonate resin of 30 to 70 mol %.

8. The polycarbonate resin according to claim 1, having a content of a remaining phenolic compound of 3000 mass ppm or less relative to 100% by mass of the polycarbonate resin.

9. The polycarbonate resin according to claim 1, wherein the structural unit (1) includes at least one of structural units represented by formulae 1 to 6:

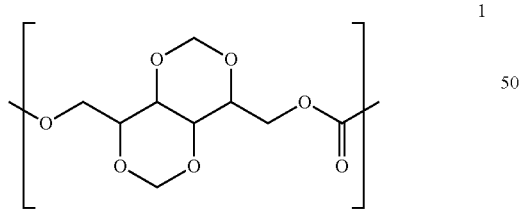

1

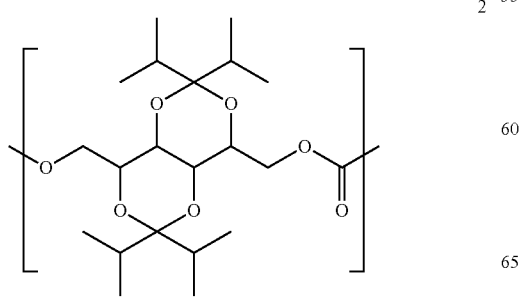

2

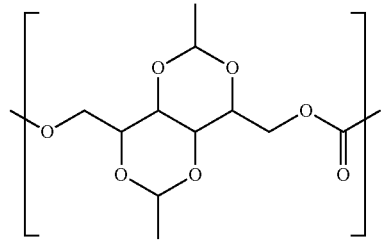

3

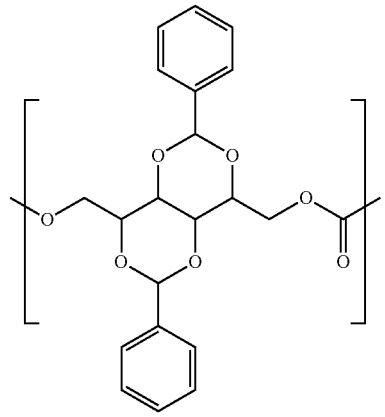

4

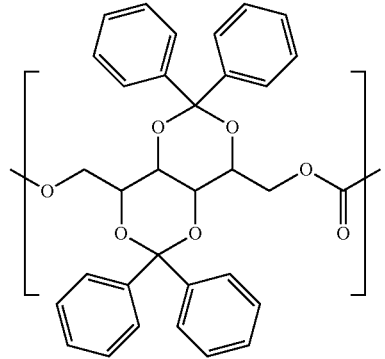

5

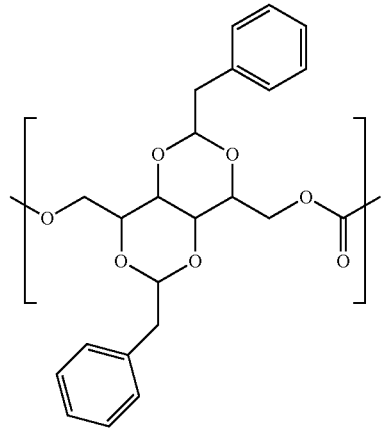

6

-continued

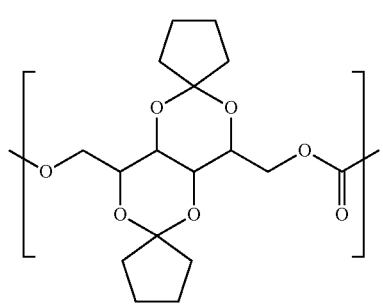

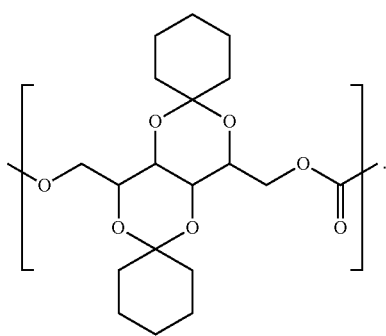

10. The polycarbonate resin according to claim 1, which has a glass transition temperature (Tg) of 80 to 250° C.

11. The polycarbonate resin according to claim 1, having a thermal decomposition temperature, as 5% weight reduction temperature, of 325° C. or higher.

12. The polycarbonate resin according to claim 1, wherein the structural unit (1) is obtained from a monomer derived from a natural sugar.

13. A polycarbonate resin composition comprising the polycarbonate resin according to claim 2.

14. A molded body obtained by molding the polycarbonate resin composition according to claim 13.

15. A method for producing the polycarbonate resin according to claim 1, which comprises performing a transesterification reaction.

16. The method according to claim 15, wherein the transesterification reaction is performed under a reduced pressure of 1 kPa or less and at a temperature of 260° C. or higher.

* * * * *